United States Patent
Hancock et al.

(10) Patent No.: US 10,434,207 B2
(45) Date of Patent: Oct. 8, 2019

(54) APPARATUS FOR STERILIZING AN INSTRUMENT CHANNEL OF A SURGICAL SCOPING DEVICE

(71) Applicant: CREO MEDICAL LIMITED, Chepstow (GB)

(72) Inventors: Christopher Paul Hancock, Bath (GB); Louis Turner, Monmouthshire (GB); Patrick Burn, Monmouthshire (GB); Sandra Swain, Stevenage (GB); Mark Ebbutt, Glewstone (GB); Simon Meadowcroft, Chippenham (GB); George Christian Ullrich, Gwynedd (GB); David Edward Webb, Gwynedd (GB); John Bishop, Monmouthshire (GB)

(73) Assignee: CREO MEDICAL LIMITED, Chepstow (GB)

( * ) Notice: Subject to any disclaimer, the term of this patent is extended or adjusted under 35 U.S.C. 154(b) by 0 days.

(21) Appl. No.: 15/971,842

(22) Filed: May 4, 2018

(65) Prior Publication Data
US 2018/0318459 A1 Nov. 8, 2018

(30) Foreign Application Priority Data

May 5, 2017 (GB) .................................. 1707230.7

(51) Int. Cl.
*A61L 2/26* (2006.01)
*H01J 37/32* (2006.01)
(Continued)

(52) U.S. Cl.
CPC ................ *A61L 2/26* (2013.01); *A61B 1/122* (2013.01); *A61B 90/70* (2016.02); *A61L 2/0029* (2013.01);
(Continued)

(58) Field of Classification Search
CPC . A61L 2/26; A61L 2/0029; A61L 2/03; A61L 2/14; A61B 90/70; A61B 1/122;
(Continued)

(56) References Cited

U.S. PATENT DOCUMENTS

| 5,105,876 A | * | 4/1992 | Burack | ................ F22B 37/003 165/11.2 |
| 2013/0261536 A1 | | 10/2013 | Sartor | |
| 2013/0289557 A1 | * | 10/2013 | Hancock | ............ A61B 18/1815 606/33 |
| 2016/0113700 A1 | * | 4/2016 | Hancock | .................. A61N 1/40 606/29 |
| 2018/0214204 A1 | * | 8/2018 | Karmarkar | ............... A61B 5/05 |

FOREIGN PATENT DOCUMENTS

| EP | 2 301 460 A1 | 3/2011 |
| EP | 2 599 506 A2 | 6/2013 |

(Continued)

OTHER PUBLICATIONS

Partial Search for International Application No. PCT/EP2018/061317 dated Aug. 30, 2018.
(Continued)

*Primary Examiner* — Nicole M Ippolito
(74) *Attorney, Agent, or Firm* — Arent Fox LLP

(57) ABSTRACT

Sterilization apparatus comprising a sterilization instrument configured to be inserted through the instrument channel of a surgical scoping device and a withdrawal device for withdrawing the sterilization instrument from the instrument channel at a predetermined rate. The sterilization instrument comprises an elongate probe having a probe tip with a first electrode and a second electrode arranged to produce an electric field from received RF and/or microwave frequency EM energy. In operation the instrument may disinfect an inner surface of the instrument channel by emitting energy while being withdrawn through the channel.

20 Claims, 12 Drawing Sheets

(51) Int. Cl.
*A61L 2/03* (2006.01)
*A61L 2/14* (2006.01)
*A61L 2/00* (2006.01)
*A61B 1/12* (2006.01)
*A61B 90/70* (2016.01)

(52) U.S. Cl.
CPC .............. *A61L 2/03* (2013.01); *A61L 2/14* (2013.01); *H01J 37/3244* (2013.01); *H01J 37/32348* (2013.01); *H01J 37/32366* (2013.01); *H01J 37/32394* (2013.01); *A61B 2090/701* (2016.02); *A61L 2202/11* (2013.01); *A61L 2202/24* (2013.01); *H01J 2237/336* (2013.01)

(58) Field of Classification Search
CPC ........... H01J 37/32348; H01J 37/32366; H01J 37/32394; H01J 37/3244
USPC ........................ 250/453.11, 454.11, 455.11
See application file for complete search history.

(56) References Cited

FOREIGN PATENT DOCUMENTS

| | | |
|---|---|---|
| GB | 2464501 A | 4/2010 |
| GB | 2487199 A | 7/2012 |
| GB | 2520197 A | 5/2015 |
| GB | 2521611 A | 7/2015 |
| WO | WO 2009/060213 A1 | 5/2009 |
| WO | WO 2011/055368 A2 | 5/2011 |
| WO | WO 2014/184544 A1 | 11/2014 |
| WO | WO 2016/071680 A1 | 5/2016 |
| WO | WO 2017/149072 A2 | 9/2017 |

OTHER PUBLICATIONS

Search Report for United Kingdom Application GB1707230.7 dated Nov. 6, 2017.

\* cited by examiner

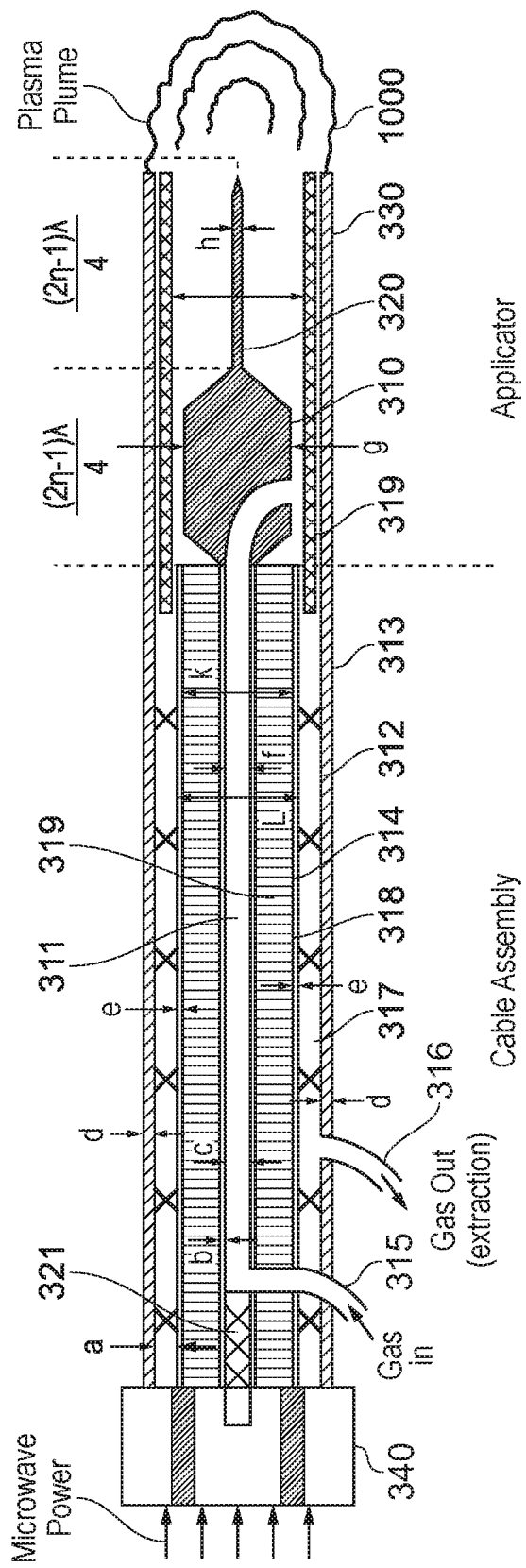
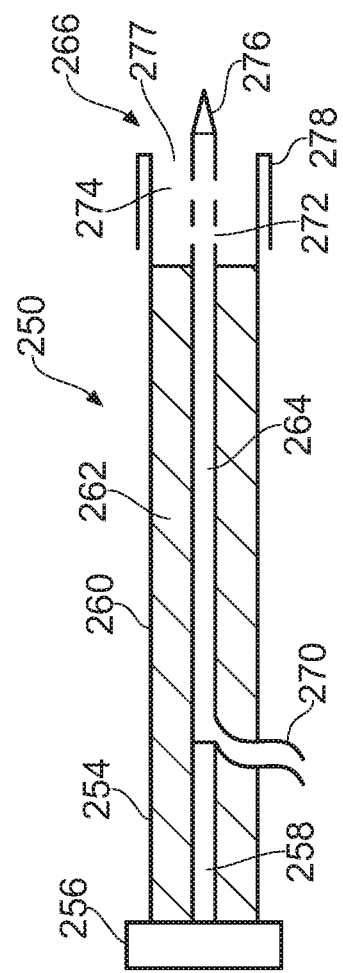
FIG. 9
FIG. 10

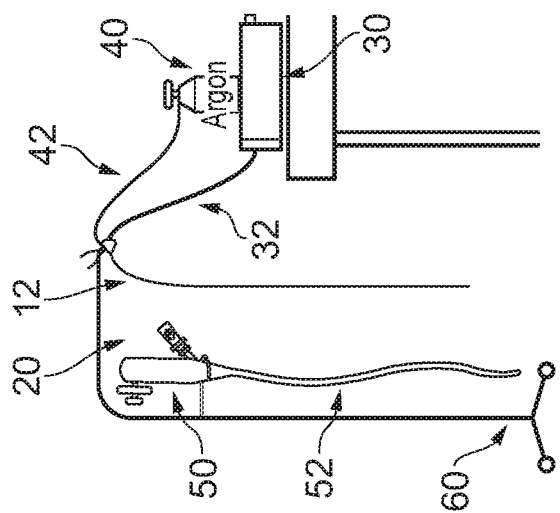
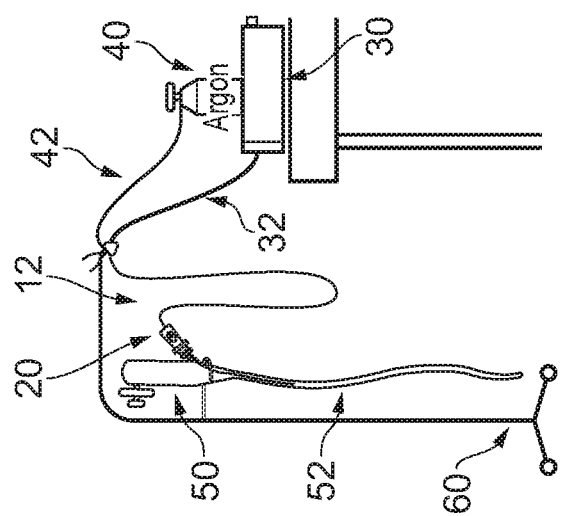
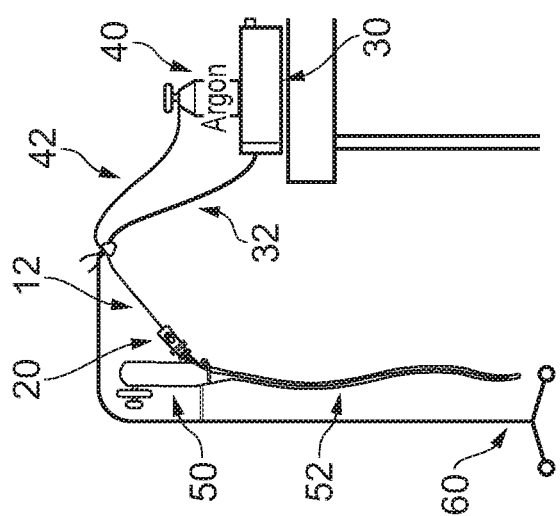
FIG. 17A
FIG. 17B
FIG. 17C

APPARATUS FOR STERILIZING AN INSTRUMENT CHANNEL OF A SURGICAL SCOPING DEVICE

CROSS-REFERENCE TO RELATED APPLICATIONS

This application claims priority to Great Britain Patent Application No. 1707230.7, filed May 5, 2017. The disclosure of the priority application is incorporated in its entirety herein by reference.

FIELD OF THE INVENTION

The present invention relates to sterilization of surgical scoping devices such as endoscopes. In particular, the invention relates to an apparatus which can be used to sterilize or disinfect the instrument channels of such surgical scoping devices.

BACKGROUND OF THE INVENTION

Bacteria are single-celled organisms that are found almost everywhere, exist in large numbers and are capable of dividing and multiplying rapidly. Most bacteria are harmless, but there are three harmful groups; namely: cocci, spirilla, and bacilla. The cocci bacteria are round cells, the spirilla bacteria are coil-shaped cells, and the bacilli bacteria are rod-shaped. The harmful bacteria cause diseases such as tetanus and typhoid.

Viruses can only live and multiply by taking over other cells, i.e. they cannot survive on their own. Viruses cause diseases such as colds, flu, mumps and AIDS. Fungal spores and tiny organisms called protozoa can cause illness.

Such micro-organisms are known to persist in the instrument channel of surgical scopes (such as endoscopes, gastroscopes etc.), and it is desirable to remove these organisms. Sterilization is an act or process that destroys or eliminates all form of life, especially micro-organisms.

Known methods of sterilizing the instrument channels of scopes involve the use cleaning fluids which are flushed through the channel to expel debris. A brush may also be used to scrub the interior. The scope is then disinfected in automatic washing or disinfection units, which may involve the immersion of the scope in potentially harmful chemicals such as glutaraldehyde. Finally, the scope is rinsed thoroughly with water, then alcohol, to remove traces of the disinfectant.

Such known methods are labor-intensive, and are also prone to incomplete or insufficient sterilization of the instrument channel. The present invention aims to address these issues.

SUMMARY OF THE INVENTION

According to a first aspect of the invention, there is provided sterilization apparatus for sterilizing an instrument channel of a scope device. The apparatus comprises a sterilization instrument configured to be inserted through the instrument channel of a surgical scoping device (also referred to herein as simply a "scoping device") and a withdrawal device for withdrawing the sterilization instrument from the instrument channel at a predetermined rate. The sterilization instrument comprises an elongate probe comprising a coaxial cable for conveying radiofrequency (RF) and/or microwave frequency electromagnetic (EM) energy, and a probe tip connected at the distal end of the coaxial cable for receiving the RF and/or microwave energy. The coaxial cable comprises an inner conductor, an outer conductor, and a dielectric material separating the inner conductor from the outer conductor. The probe tip comprises a first electrode connected to the inner conductor of the coaxial cable, and a second electrode connected to the outer conductor of the coaxial cable, wherein the first electrode and second electrode are arranged to produce an electric field from the received RF and/or microwave frequency EM energy.

In this way, the first aspect of the invention provides the ability to perform sterilization at the distal end of an instrument, in particular for the purpose of disinfecting the instrument channel of surgical scoping device, such as an endoscope, gastroscope, bronchoscope or the like. The apparatus allows the instrument channel to be thoroughly sterilised using RF and/or microwave frequency EM energy, which is supplied to the probe tip from a generator.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

In this specification "microwave frequency" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz. The microwave frequency may be adjusted to enable the microwave energy delivered to be optimised. For example, a probe tip may be designed to operate at a certain frequency (e.g. 900 MHz), but in use the most efficient frequency may be different (e.g. 866 MHz).

The elongate probe may be dimensioned to be insertable through a scoping device, e.g. through the instrument channel of an endoscope, gastroscope, bronchoscope, colonoscope or the like. For example, the coaxial cable may have a diameter of 2.5 mm or less, preferably 2.2 mm or less. The coaxial cable may have a sleeve, wherein the sleeve may have an outer diameter less than 2.6 mm, preferably less than 2.5 mm. For larger laparoscopic instruments, the outer diameter may be 3 mm or more, and larger diameter co-axial cable may be used. The coaxial cable may have a length of around 2 m or more to ensure that the probe can extend through the entire length of the instrument channel. For example, in colonoscopes, the instrument channel may be around 1.8 m in length.

The first electrode may be a radiating microwave monopole antenna structure coupled to receive RF and/or microwave EM energy from the coaxial cable. The outer conductor of the coaxial cable may be grounded to form an unbalanced feed or may be floating to form a balanced feed to the antenna, i.e. where the voltage on both conductors is going up and down. Preferably the first electrode is shaped to act as a microwave antenna for emitting a microwave field corresponding to the received microwave EM radiation.

Herein, the term "inner" means radially closer to the center (e.g. axis) of the instrument channel and/or coaxial cable. The term "outer" means radially further from the center (axis) of the instrument channel and/or coaxial cable. The term "conductive" is used herein to mean electrically conductive, unless the context dictates otherwise. Herein, the terms "proximal" and "distal" refer to the ends of the elongate probe. In use the proximal end is closer to a generator for providing the RF and/or microwave energy, whereas the distal end is further from the generator.

Preferably the sterilization instrument further comprises a gas conduit for conveying gas to the probe tip, wherein the first electrode and second electrode may be arranged to produce an electric field from the received RF and/or microwave frequency EM energy across a flow path of gas received from the gas conduit to produce a thermal or non-thermal plasma. The thermal or non-thermal plasma may be used to provide a reduction in bioburden for a range of bacteria, including methicillin-resistant *Staphylococcus aureus* (MRSA), *Clostridium difficile* (c. diff.; both spores and vegetative state) and *Escherichia coli* (*E. coli*), and so may allow for more efficient and thorough sterilization of the instrument channel. The instrument may also be configured to produce a combination of non-thermal plasma and non-ionising microwave radiation.

In some embodiments the coaxial cable has a lumen extending from a proximal end to a distal end of the cable, wherein the lumen may form the gas conduit for conveying gas through the elongate probe to the probe tip. Such arrangements may make the sterilization instrument more compact, such that energy and gas may be conveyed down the sterilization instrument to the probe tip independently of any control line or feed line that runs through the instrument channel. Accordingly, these arrangements may increase the space available for additional supplies or components (e.g. control wires) to be used with the sterilization instrument. Moreover, these arrangements may reduce or eliminate the effect that additional supplies or components have on energy conveyed by the coaxial cable.

The gas conduit may have an input port located at a proximal end of the sterilization instrument for connecting to a source of gas (e.g. a pressurised gas canister or the like). The gases that are of interest for implementation of the apparatus disclosed herein are: air, helium, argon, nitrogen, compressed air, and carbon dioxide. The system need not be limited to these gases. Gas mixtures may be used, e.g. various concentration of argon, air and helium may be used, e.g. 1% air and 99% helium, or 5% air and 95% helium. To provide directivity to the gas feed, compressed air may be used.

The apparatus may include a flow controller arranged to adjustably control gas flow in the gas conduit. The gas flow rate may affect the size of the plasma plume or the plasma energy; this may be controlled by the flow controller. Preferably the gas conduit passes through the probe tip. This may aid the generation of plasma in the vicinity of the first and second electrodes at the probe tip. In some embodiments, the gas conduit may be arranged to ensure that the plasma plume extends outside the probe tip to contact the surface to be sterilised.

The plasma may be struck using RF or microwave energy, which may be received as a high voltage pulse. Microwave energy may be used to sustain the plasma after it is struck, i.e. deliver power into the plasma to maintain the state of ionization. This may also be received as a pulse. This arrangement may prevent electric field collapse due to the capacitance of the cable and loading variations, e.g. due to changing from a dry to a wet environment at the probe tip. Striking the plasma for delivery out of the probe tip using microwave frequency energy may be possible, e.g. by using a microwave resonator or an impedance transformer, i.e. a quarter wave transformer that transforms a low voltage to a higher voltage to strike plasma using a higher impedance transmission line that is a quarter wave (or an odd multiple thereof) long at the frequency of operation. This high impedance line may be switched in to strike plasma and switched out (i.e. to return to a lower impedance line) once the plasma has been struck and it is required to sustain plasma. A power PIN or varactor diode may be preferably used to switch between the two states, although it may be possible to use a coaxial or waveguide switch. The high electric field for striking the plasma may be caused by creating a high impedance condition for either the RF EM energy or the microwave EM energy at the probe tip. This can be achieved through the selection of a suitable geometry for the first and second electrodes. For example, a piece of insulating dielectric material, such as quartz or other similarly low loss material, may be located between the first and second electrodes. This may increase the impedance and therefore facilitate the creation of a high electric field.

To strike plasma it is desirable to have a high electric field (e.g. high voltage condition). In the plasma strike state (i.e. before the plasma exists) the gas is non-conducting and therefore has high impedance. In order to strike plasma, it is necessary to set-up the high impedance state at the distal end of the probe tip or within the probe tip in order to enable the high voltage (high electric field) necessary to break down the gas to be generated. The apparatus of the invention may permit the magnitude of microwave power delivered to the plasma to be controlled, e.g. through modulation of the microwave signal and control of amplifier gain or control of the level of input signal to an amplifier with fixed gain, as well as the efficiency by which it is delivered, e.g. through dynamic impedance matching. This arrangement may also enable the dosage of plasma energy delivered into the surface to be sterilised to be accurately quantified.

The impedance of the plasma is preferably matched to the impedance of the probe tip (and energy delivery system) at the frequency of the microwave energy to enable efficient transfer of the microwave energy, produced by the generator, into the plasma. Where microwave energy is used, the probe tip and/or generator may be tuned (statically or dynamically) to ensure that the plasma is matched into the load presented by the instrument channel and material within the channel. At microwave frequencies, the coaxial cable forms a distributed element transmission line, where the impedance match between the probe tip and energy source is determined by the source impedance of the microwave generator, the characteristic impedance of the coaxial cable (transmission line), and the impedance of the probe tip structure itself. If the characteristic impedance of the coaxial cable is the same as the output impedance of the source then all of the microwave power will be delivered into the probe tip, less the attenuation caused by the coaxial cable (dielectric and conductor losses). If the impedance of the probe tip and the instrument channel is the same as the characteristic impedance of the coaxial cable, then the maximum power available at the source will be transferred into the plasma/instrument channel load. Adjustments may be made to probe tip structure in order to maintain the best impedance match between the probe tip and the plasma/instrument channel load, as explained below. Adjustments may also be made at the generator or at the interface between the distal end of the first cable and the proximal end of the second (instrument) cable. These adjustments may be in the form of a change of capacitance and/or inductance of a matching network, i.e. stub tuning.

The apparatus may use, as a generator, a source oscillator to produce a low power microwave frequency signal and a power amplifier (e.g. an arrangement of microwave transistors) to amplify the low power signal to a level that is high enough to enable an electric field to be produced which is required to strike the plasma using a gas found to be suitable for the particular application. Solid state signal amplifiers may be used. The system may also operate in a mode whereby the amplifier is driven into saturation or full power to set up an electric field necessary to strike the plasma and then backed off once it has been struck. The ability to control the microwave energy can enable a plasma to be generated that is most suitable for any one of a variety of applications of interest. Control of the microwave energy and/or the gas flow rate and/or the gas mixture gives control over the size of the plume and the temperature at the inner surface of the instrument channel being treated. Furthermore, the system may be arranged to quantify the dosage of plasma energy delivered to the surface to be treated. The microwave energy may be controlled by any one or more of varying a frequency of the microwave energy in a controlled manner (e.g. controlling the frequency of radiation from the microwave radiation generator), varying the power level in a controlled manner, and modulating the microwave energy in a controlled manner. The generator may include a microwave signal modulator arranged to modulate the microwave energy delivered to the probe tip. The modulation frequency may be contained within the range from 0.1 Hz up to 10 MHz. The duty cycle may be from less than 1% to 100%. In some embodiments, the modulation frequency may be from 10 Hz to 100 kHz and the duty cycle may be between 10% and 25%. In preferred embodiments the modulation frequency may be between 100 Hz and 1 kHz, and the duty cycle may be 20%.

The apparatus may thus be arranged to generate the plasma using pulsed operation. In one embodiment, the plasma may be struck on each pulse (the strike may occur due to a transient produced on one of the edges of the pulse—normally the positive going edge). The operation of the system may be such that it is necessary to keep applying pulses to the system in order to generate the required effects.

In some embodiments, the probe tip may be a plasma applicator having an enclosed plasma generating region and an outlet for directing plasma out of the plasma generating region towards an inner surface of the instrument channel. The plasma applicator may direct and/or focus the plasma using suitable antenna arrangements that are designed and developed specifically to enable a suitable plume of plasma, or a plurality of plumes, to be created and delivered in such a manner that controlled thermal/non-thermal plasma may be produced that is useful for destroying various types of bacteria or viruses or fungi. In one embodiment, the plasma applicator may be arranged selectively to emit plasma (ionising radiation) and microwave (non-ionising) radiation. The apparatus may thus emit plasma only, microwave energy only, or a mix of the two.

Coaxial arrangements may be used as applicators to create the plasma. For example, a plasma applicator may comprise a coaxial assembly having an inner conductor surrounded by and separated from an outer conductor, wherein the inner conductor tapers at its distal end to concentrate an electric field in the plasma generating region to promote striking plasma when gas and microwave energy are delivered thereto. The coaxial assembly may include a plurality of voltage transformers each having different impedance, the plurality of voltage transformers being arranged to concentrate an electric field in the plasma generating region. Each voltage transformer may comprise a section of the coaxial assembly having a length that is a quarter wavelength of the microwave energy carried thereby from the microwave generator and wherein the impedances of the plurality of voltage transformers can be set by selecting the outer diameter of the inner conductor in each section of the coaxial assembly.

Quarter wave (or an odd number thereof) impedance transformers may be realised in coaxial or waveguide systems and the specific structure used may be determined by the specific application and the environment in which it is desired to generate the plasma. In one embodiment, the system may comprise a solid state source, a tuner and simple fixed impedance (e.g. 50Ω) applicator structure to create and sustain plasma. In another embodiment, the system may not include a tuner, but may have a voltage transformer in the applicator (created e.g. using a plurality of impedance transformers) to strike the plasma and then keep striking to create a quasi-continuous plasma. Repeated plasma strikes may be beneficial to regulating the plasma temperature. To create the plasma, the plasma applicator may include igniters which may be made from ceramic/intermetallic material or piezo-igniters which generate a high voltage spark based on the impact of a spring driven hammer arrangement on the piezoelectric ceramic material. Once the plasma has been struck, or initiated, the microwave energy may then be used to enable the plasma to be sustained or maintained. Tuning elements within the instrument or within the generator may be used to facilitate this.

The plasma applicator may include one or more resonator structures made from tungsten or another material that can withstand high temperatures. For example, the resonant structure may include a tungsten rod or needle coated with a material that is a good conductor, i.e. silver, copper or gold. As an example, silver nitrate may be used to electroplate the needle with silver or copper sulphate used to coat with copper. Other low loss conductors may be used, e.g. copper, aluminum, silver coated stainless steel, etc., which have a small length of tungsten crimped to the distal end where the plasma is to be generated. Quartz tubes or quartz slices may be used inside the structure for the purpose of intensifying the electric field generated between the inner and outer electrode in a coaxial applicator arrangement by effectively bringing the two conductors closer together. The quartz tube also prevents arcing between the two conductors, which helps to produce a uniform beam of plasma. It is preferable to use a low loss quartz material.

The plasma applicator may include sensing means at its distal end which is arranged to provide information concerning the plasma to enable adjustments (if needed) to take place, i.e. spectral content (wavelengths), plasma energy and plasma temperature. For example, the plasma applicator may include any of a temperature sensor, a calorimeter, one or more photo detectors for monitoring a spectral content of the plasma produced at the distal end of the applicator. The information obtained from these sensors may be used in a feedback loop to control the plasma produced at the output of the system, i.e. control the microwave power level, the duty cycle, the waveform of the microwave power, the gas flow rate, the gas mixture, the gas timing, etc.

In some embodiments, where the probe tip is a plasma applicator, a DC field or DC voltage level may be applied to the microwave field in the plasma generating region. In a particular arrangement, a bias 'T' may be used at the input to the plasma applicator or the antenna and the DC voltage applied through an inductor, whereas the microwave field may be applied through a capacitor. In this arrangement, the inductor will pass the DC voltage but block the high frequency microwave signal. The inductive reactance is given by $2\pi fL$ (where f is the frequency of the microwave energy and L is the inductance of the inductor). If the frequency is zero (i.e. DC), and inductance has a finite value, the impedance tends to zero. The capacitor will pass the high frequency microwave signal but block the DC voltage. The capacitive reactance is given by $1/(2\pi fC)$ (where C is the capacitance of the capacitor). If the frequency tends to infinity (e.g. 400 MHz or more) and the capacitance has a finite value, the impedance tends to zero. The DC voltage may be used to initiate or strike the plasma and the microwave field may be used to sustain the plasma. A fixed tuning stub or a plurality of tuning stubs may also be arranged as a band reject filter to replace the inductor and be used to block or stop the high frequency signals getting back into the low frequency or DC generator.

In some embodiments, the sterilization instrument may also be configured for use as an electrosurgical instrument. An electrosurgical instrument may be any instrument, or tool, which is used during surgery and which utilizes RF or microwave energy. This means that the same device which is used for sterilization of the instrument channel may be used for invasive or non-invasive electrosurgery such as coagulation (e.g. in treating peptic ulcers or coagulation of large blood vessels), tissue resection, or other open and keyhole or laparoscopic procedures. In this way, the sterilizing function may also be used to sterilize body cavities before or after treatment. Further, the sterilization instrument may also be configured to produce non-thermal plasma, thermal plasma and non-ionising microwave radiation where it is to be used in NOTES procedures or where it is advantageous to be able to perform surface coagulation, sterilization of body tissue and deep coagulation of large vessels or bleeders.

Preferably, the coaxial cable comprises a layered structure comprising: an innermost insulating layer; an inner conductive layer formed on the innermost insulating layer; an outer conductive layer formed coaxially with the inner conductive layer; and a dielectric layer separating the inner conductive layer and the outer conductive layer, wherein the inner conductive layer, the outer conductive layer and the dielectric layer form a transmission line for conveying RF and/or microwave frequency energy, and wherein the innermost insulating layer is hollow to form a channel through the sterilization instrument. The diameter of the channel formed in the innermost insulating layer is preferably 3 mm or less, e.g. 2.8 mm. The channel may form the gas conduit for conveying gas to the probe tip.

The layer-structured coaxial cable may include, e.g. at a distal end thereof, a first terminal that is electrically connected to the inner conductive layer and which extends through the innermost insulating layer into the channel, and a second terminal that is electrically connected to the outer conductive layer and which extends through the dielectric layer and innermost insulating layer into the channel. The first terminal and the second terminal may be arranged to form electrical connection (e.g. physically engage) corresponding contacts formed on a probe tip that is insertable in or through the channel. The first terminal and the second terminal may be formed at the distal end of the inner conductive layer and outer conductive layer respectively. The outer conductive layer may extend longitudinally further in a distal direction than the inner conductive layer, whereby the first terminal is located proximally from the second terminal. In such embodiments, the probe tip may include a connection collar having a first contact for connecting to the first terminal and a second contact for connecting to the second terminal. The first contact and the second contact may be electrically connected to the first electrode and the second electrode respectively.

The probe tip may be introduced to the distal end of the channel via a catheter that is fed through the channel. A connection collar may be mounted on the catheter, and may comprise a cylindrical body having a diameter greater than the diameter of the catheter. The outer surface of the cylindrical body may be in close proximity (e.g. touching) the innermost layer of the layer-structured coaxial cable, to ensure secure engagement between the first contact and first terminal and between the second contact and second terminal. The first terminal and second terminal may project inwards from the innermost layer slightly. The connection collar may include a shoulder for abutting a stop flange at the distal end of the coaxial cable to securely locate the collar in position. The probe tip may include an extension sleeve that extends axially away from the connection collar. In use, the extension sleeve may thus protrude out of the end of the channel. The extension sleeve may comprise a tube of dielectric material, and may carry conductive structures (e.g. conductive rods or the like) which provide electrical connection between the first contact and first electrode and between the second contact and second electrode respectively. The conductive structure may comprise a short length of conventional coaxial cable.

If the probe tip is arranged to receive RF energy from the layer-structured coaxial cable, it may be desirable to prevent voltage breakdown from occurring between the inner conductive layer and outer conductive layer. This may be achieved by using a material with a high breakdown threshold (e.g. Kapton® polyimide tape) as the dielectric layer. Alternatively, if the probe tip is arranged to receive both RF energy and microwave energy from the layer-structured coaxial cable, it may be desirable to create separate pathways for the RF energy and microwave energy, because low loss dielectric material suitable for supporting microwave energy propagation may not have a high enough breakdown threshold to safely insulate conductors carrying RF energy. Accordingly, the layer-structured coaxial cable may include an additional conductor which forms a first pole of an RF-carrying bipolar transmission line, and wherein the inner conductive layer and the outer conductive layer form a second pole of the RF-carrying bipolar transmission line. For example the additional conductor may be a conductive wire carried within the instrument channel. In this arrangement, the innermost insulating layer may be made of a material (e.g. polyimide) with the required breakdown properties. Where an additional conductor is provided to carry the RF energy, the inner conductive layer and outer conductive layer of the layer-structured coaxial cable may be electrically connected (shorted) at the proximal end thereof.

With an arrangement such as this it may be necessary to provide a configuration, such as a diplexer, at the distal end of the layer-structured coaxial cable to prevent the higher voltage radiofrequency signal from travelling back along the inner conductive layer and outer conductive layer, and/or to prevent the microwave signal from travelling back along the additional conductor.

The dielectric layer may comprise a solid tube of dielectric material or a tube of dielectric material having a porous structure. Being a solid tube of dielectric material may mean that the dielectric material is substantially homogeneous. Having a porous structure may mean that the dielectric material is substantially inhomogeneous, with a significant number or amount of air pockets or voids. For example, a porous structure may mean a honeycomb structure, a mesh structure, or a foam structure. The dielectric material may comprise PTFE, or another low-loss microwave dielectric. The dielectric material may comprise a tube with a wall thickness of at least 0.2 mm, preferably at least 0.3 mm, more preferably at least 0.4 mm, e.g. between 0.3 and 0.6 mm.

The inner conductive layer and/or the outer conductive layer may comprise: a metal coating on the inside or outside of a tube of material; a solid tube of metal positioned against the inside or outside of a tube of material; or a layer of braided conductive material embedded in a tube of material. The inner conductive layer and/or the outer conductive layer may comprise a silver coating. The inner conductive layer and/or the outer conductive layer may have a thickness of approximately 0.01 mm.

Instead of being projections, one or both of the first terminal and the second terminal may comprise a recess, e.g. formed in the innermost insulating layer. The connection collar (discussed above) for example formed in an end face of the cable, for receiving a corresponding conductive protrusion on an end face of the probe tip.

In one configuration the layer-structured coaxial cable may be fabricated as a plurality of layers, e.g. a hollow inner tubular layer (the innermost insulating layer); a layer of conductive material on an outer surface of the hollow inner tubular layer (inner conductive layer); a tube of dielectric material on an outer surface of the conductive material (dielectric layer; and a layer of conductive material on an outer surface of the tube of the dielectric material (outer conductive layer). The structure may, or may not, comprise air gaps between some or all of these layers. An advantage of avoiding air gaps is that losses in the cable may be minimized. In one example, this structure could be manufactured by sequentially coating each subsequent layer over the preceding (inner) layer.

Alternatively, this structure could be made by forming one or more of the layers as a first part and one or more of the layers as a second part, and then sliding one part inside of the other. The hollow inner tubular layer preferably comprises polyimide, but may be PTFE or other suitable insulating material. The hollow inner tubular layer may have a thickness of 0.1 mm.

In some embodiments, the probe tip may comprise an extension of the innermost insulating layer, e.g. an innermost PTFE tube, and the inner conductive wrap of the layer-structured coaxial cable, and the channel may extend through the probe tip. A dielectric cylinder may be placed over the inner conductor, and the inner conductor which passes through the dielectric cylinder may be considered the first electrode of the probe tip. The second electrode may preferably be a metal cylinder, e.g. a thin wall metal tube, preferably copper, which is electrically connected to the outer conductor of the layer-structured coaxial cable, for example by sliding over the dielectric cylinder and a portion of the outer conductor. The probe tip may have a dielectric wall thickness of 0.325 mm, an outer diameter of 2.5 mm and a channel diameter of 1 mm.

The dielectric cylinder and second electrode may be set up to be of a length equal to a quarter wavelength at the frequency of operation (e.g. 2.45 GHz). The dielectric material may also be chosen to provide a good impedance match with the low impedance environment created by the plasma. Preferably, the probe tip has a maximum length of 12 mm to enable easy access to the instrument channel. Even more preferably, the dielectric material has a dielectric constant of 5 or more.

The elongate probe may alternatively be configured to have a reduced channel diameter through the probe tip to increase impedance of the probe tip and allow a dielectric material with a lower dielectric constant to be used. In some embodiments, the first electrode may be a first conductive cylinder, such as a thin wall metal tube, preferably copper, which is inserted at least partially into the innermost insulating layer of the coaxial cable. The first electrode may be connected to the inner conductive layer of the coaxial cable. A dielectric cylinder may be positioned over the first electrode. Preferably, the second electrode comprises a second conductive cylinder, e.g. a thin wall metal tube, preferably copper, which is coaxial with the first electrode and dielectric cylinder, and which is electrically connected to the outer conductor of the layer-structured coaxial cable. The probe tip may have an outer diameter of 2.5 mm, a channel diameter of 0.8 mm and a dielectric wall thickness of 0.65 mm.

Preferably, the inner conductor of the layer-structured coaxial cable is a tight fit into the dielectric cylinder. In some embodiments, the dielectric cylinder may have a number of holes in the cylinder walls to make it easier to strike the plasma. The closer the first and second electrodes of the probe tip are, the easier it is to strike the generated plasma, as this is a function of the breakdown of the gas and the electric field produced between the electrodes—assuming that the voltage is fixed at a peak Vmax (determined by the generator), the only way to increase the electric field is to reduce the distance between the electrodes.

In one embodiment, the probe tip may have a coaxial structure that has a plasma generating region with a diameter of between 3 mm and 5 mm; i.e. the inner diameter of the second electrode within the coaxial structure may have a diameter of between 3 mm and 5 mm, and a quartz tube that fits tightly inside may have a wall thickness of between 0.25 mm and 1 mm, and where the outer diameter of the first electrode may be between 0.75 mm and 4 mm (allowing a space for gas to flow in the region between the inner conductor and the inner wall of the quartz tube), a non-thermal plasma suitable for disinfection or sterilization may be produced by operating the generator in pulsed mode with a duty cycle of less than 40%, i.e. 28%. In one embodiment, the rms power in a single microwave pulse is 50 W and the pulse ON time is 40 ms, within a total period of 140 ms, i.e. the average power delivered into the plasma is 14.28 W at 2.45 GHz. When an RF strike pulse is used in this configuration, the duration of the RF strike pulse is around 1 ms, and the frequency of the sinusoidal oscillations is 100 kHz. The amplitude is around 1 kV peak (707 $V_{rms}$). The RF power is less than 10% of the microwave power. The RF pulse may be synchronized to the microwave burst or pulse and triggered on the rising edge of the microwave burst or pulse.

To produce thermal plasma, the duty cycle may be increased, i.e. to 50% or continuous wave (CW) and/or the rms power level may be increased, i.e. to 75 W or 100 W for this particular probe tip geometry (if the geometry is decreased or increased then the microwave power and the amplitude of the RF strike pulse would be adjusted accordingly). The ratio of RF to microwave power will preferably remain constant, i.e. less than 10% for non-thermal and thermal plasma.

In some embodiments, the outer electrode of the coaxial cable may be connected to the second electrode by a conductive mesh that permits gas to flow through it. The conductive mesh may therefore be mounted in the gas conduit of the instrument, which in some embodiments may be the space between the coaxial cable and the sleeve. In such embodiments, the space between the coaxial cable and the sleeve may alternatively be divided into a plurality of sub-conduits, e.g. by divider elements connected to or part of the sleeve. In this situation, the divider elements or a separate connector element may provide an electrical connection between the outer conductor of the coaxial cable and the second electrode. The connection may also be made by one flexible wire or strip, which may be soldered or crimped to the second electrode.

In some embodiments, where the sterilization instrument is configured for use as an electrosurgical instrument, the gas conduit may be configured to convey liquid through the elongate probe to the probe tip. This is useful in surgical procedures where fluid (e.g. saline) may be used to plump up biological tissue or flush the treatment region, e.g. to remove waste products or removed tissue to provide better visibility when treating; particularly in endoscopic procedures. The proximal end of the gas conduit may terminate with a connector that allows it to be attached to a syringe used to store and introduce liquid into the conduit. Where the gas conduit is provided as a lumen through the elongate probe, the lumen or channel may comprise multiple lumina such that the coaxial cable may convey gas to the probe tip, or both gas and liquid to the probe tip through the plurality of lumina.

The probe tip may have any one of the structures described herein, such as:

A unitary body (i.e. a single piece of metallized dielectric material, e.g. ceramic or the like) suitable for use in open surgery and key-hole (laparoscopic) surgery as well as instrument channel sterilization; and A parallel plate structure (i.e. a planar transmission line element) having a body of substantially planar dielectric material, the first electrode being a first conductive layer on a first surface of the planar element, and the second electrode being a second conductive layer on a second surface of the planar element that is opposite to the first surface.

The unitary body may have a shape that conforms to a treatment target area or to perform a desired function. For example, the probe tip may be curved to follow the wall of the bowel, or may be hooked to facilitate tissue removal in use as an electrosurgical instrument.

Where the parallel plate structure is used, the gas conduit may be arranged to introduce gas between the first and second conductive layers (which may be formed a two independent plates) to create non-thermal or thermal plasma that can be used to provide the return path for the RF current in sterilization, or in electrosurgery. The planar transmission line element may contain a both a region of dielectric material with a high dielectric constant to provide the local return path and a second open region that can be filled with gas to enable non-thermal plasma to be produced for sterilization or for thermal plasma to be produced for tissue cutting or surface coagulation to be performed in electrosurgery. This arrangement may also take advantage of the use of a material with a high relative permittivity (or dielectric constant) inserted between the two conductive layers or plates (active and return conductors). The high permittivity material increases the capacitance of the structure, which in turn reduces the impedance of the structure in a linear manner, thus helping to ensure that the preferential return path for the RF current is set up or exists between the two plates. When the plasma is removed, the structure looks like a parallel plate transmission line with air separating the two plates. This arrangement may be used to efficiently radiate microwave energy along one or more of the edges of the structure and/or through a single or plurality of slots or apertures contained within one or more of the surfaces. The parallel plate structure without plasma may also be used to set-up the conditions necessary for RF sterilization or electrosurgery (e.g. cutting and microwave coagulation), i.e. at RF the structure can be modelled as a parallel plate capacitor with a dielectric material sandwiched between the two plates with layers of metallization coming to the edges along the length of the blade and cut back at the ends and at microwave frequency, the structure may be modelled as a distributed element transmission line structure capable of radiating microwave energy from one or both long edges and/or from the distal end.

The parallel plate structure with a layer of metallization on both sides of the dielectric material may be used to efficiently perform RF sterilization or tissue cutting in a most efficient manner when the respective layer of metallization comes right to the edge of the dielectric material, i.e. no dielectric material is exposed on the surfaces and only metal can be seen. The dielectric can also be exposed such that microwave sterilization, ablation or coagulation can be performed along the edges or at the end of the structure. It may be preferable to remove a small amount of metallization at the distal end of the structure, i.e. 0.5 mm to 1 mm from the end, in order to prevent the device from cutting into tissue at the end if that is undesirable.

In one embodiment, the parallel plate structure may be configured as follows:

(i) a first dielectric material comprising a block having a width of 1.5 mm to 2 mm, length of 6 mm to 12 mm;

(ii) the first and second electrodes comprise layers of metallization on the opposite surfaces of the first dielectric material that extends to the edges on both sides of the dielectric along the length of the blade, the overall thickness of the block with layers of metallization being 0.3 mm to 0.5 mm;

(iii) a 0.5 mm gap in the metallization forming the first electrode at the proximal end of the first dielectric material for matching and to prevent the active conductor being shorted out;

(iv) a 0.2 mm to 1 mm gap in the metallization forming the first and second electrodes at the distal end of the first dielectric material to prevent the structure from cutting tissue; and (v) a small radius of approximately 0.2 mm on the corners of the distal end of the first dielectric material to prevent the structure from getting stuck inside the instrument channel due to the sharp edges snagging on the inner walls.

Where the sterilization instrument is used to emit thermal or non-thermal plasma, a slot or plurality of slots may be provided to allow the hot gas to escape from the structure to create the effect. Non-thermal plasma may be radiated from said slots in order to enable the same device to be used to sterilize tissue or kill bacteria within or on the surface located in the vicinity of the probe tip, i.e. within the instrument channel.

The probe tip may comprise a plurality of planar transmission line elements arranged in parallel, the plurality of planar transmission line elements received the RF signal and the microwave signal from the coaxial cable via a balanced power splitter arrangement. The balanced power splitter may ensure that the RF and microwave signals are received by plurality of transmission line elements in phase, so that the total emitted energy is uniform.

The probe tip may include a quarter wavelength transformer (i.e. a connector having an electrical length equal to an odd multiple of a quarter of the wavelength at the frequency of operation) connected between the coaxial cable and the plurality of planar transmission line elements to impedance match the coaxial cable to the plurality of planar transmission line elements.

Preferably the probe tip extends beyond the coaxial cable by 8 mm or less, optimally by 5 mm or less, and may have a width of 1.8 mm or less, optimally 1.5 mm or less, and a thickness of 0.5 mm or less, optimally about 0.3 mm.

The first and second electrodes may form a bipolar emitting structure. The bipolar emitting structure may include a balun in the probe tip to prevent sheath currents and ensure that the microwave frequency EM field is radiated in an outwardly direction. The balun may be a simple third electrode electrically connected (e.g. soldered) to the second electrode at the distal end to form a short circuit. By making the balun a quarter-wavelength long (at the microwave frequency of operation), the short circuit condition will be transformed to an open circuit condition to prevent the flow of current along the coaxial cable. A plurality of baluns may be provided in the probe tip to increase the return loss when the probe tip is inserted into tissue. For example, one balun may increase the return loss from 15 dB to 25 dB, two baluns may take it to 40 dB and three baluns may increase it to 60 dB, i.e. one millionth of the energy emanating from the probe tip is being reflected back along the coaxial cable.

In some embodiments, the sterilization instrument may also be configured as an electrosurgical resection instrument for applying to biological tissue radiofrequency (RF) electromagnetic (EM) energy having a first frequency and microwave EM energy having a second frequency higher than the first frequency, the probe tip of the sterilization instrument comprising a planar body made of a first dielectric material having a first electrode layer on a first surface and a second electrode layer on a second surface opposite the first surface wherein the inner conductor of the coaxial cable is electrically connected to the first electrode layer and the outer conductor of the coaxial is electrically connected to the second electrode layer to enable the probe tip to receive the RF signal and the microwave signal, wherein the first and second electrode layers are arranged to act as active and return electrodes to convey RF EM radiation corresponding to the RF signal by conduction, and as an antenna to radiate microwave EM radiation corresponding to the received microwave signal, and wherein first and second electrode layers may be set back from the edges of the planar body except at an RF cutting portion located along an edge of the planar body where it is desirable to perform tissue cutting.

The probe tip may be curved in a direction between the side edges of the planar body. For example, it may have a spoon-like shape. It may be curved (or convex) at the bottom face and be curved upwards from the proximal to distal end of the structure.

In some embodiments, the gas conduit may terminate in a rigid tube or needle, e.g. a hypodermic needle, which may have a smaller diameter than the remainder of the gas conduit. The rigid tube or needle preferably includes a penetrating distal portion suitable for piercing biological tissue. This may allow fluid (saline or the like) to be injected to plump up biological tissue, for example where the instrument is used to treat the wall of the bowel. Plumping up the tissue in this manner may help to reduce the risk of bowel perforation. The same rigid tube or needle may also be used to provide gas to the probe tip, either for surgical procedures or for sterilization of the instrument channel. In one embodiment, the rigid tube or needle may be movable longitudinally relative to the probe tip, e.g. to protrude from or retract into the probe tip.

In one embodiment, Ar gas may be introduced to the probe tip through the rigid tube or needle, and a non-thermal plasma created around the edge of the probe tip. The microwave pulse ON time may be around 40 ms, with 100 ms OFF, giving a duty cycle of around 28.6%. A gated 100 kHz RF burst of around 1 kV for around 1 to 5 ms may be used, triggered by the positive edge of the 40 ms microwave pulse. The amplitude of the microwave power may be between 20 and 100 W, optimally around 60 W.

In some embodiments, the probe tip may be rotatable under the control of the sterilization instrument operator or user. In one embodiment, rotation may be achieved by turning the coaxial cable within the instrument channel, e.g. using a suitable handle or control knob. In another embodiment, the probe tip may be mounted on a rotatable plate that can turn e.g. by +/−90° relative to the instrument channel. In this arrangement, the coaxial cable may be flexible to accommodate the movement of the probe tip during rotation. The rotatable plate may be turned by a pair of control wires which each operate a pivoting lever engaged with the plate.

Any of the arrangements discussed in relation to the first aspect of the invention may preferably be used with any other conventional instrument channel cleaning methods, such as scope washing machines or sterilizers. In particular, the probe tip may further comprise a cleaning brush which may be useful in removing surgical residue from the walls of the instrument channel, particularly where such residue is not removed by EM energy and/or thermal or non-thermal plasma.

Preferably the predetermined rate of withdrawal of the sterilization instrument from the instrument channel is less than 10 mm per second. For example, the predetermined rate may be less than 5 mm per second, less than 2 mm per second or around 1 mm per second. Such a rate of withdrawal of the sterilization instrument from the instrument channel ensures that reduction in bioburden within the instrument channel is optimised.

The sterilization apparatus described herein may preferably be used in conjunction with additional apparatus which is configured to also sterilize the external surfaces of a scoping device. For example, the additional apparatus may comprise a treatment chamber into which the scoping device can be loaded. Preferably, the treatment chamber is configured to subject the external surfaces of the scoping device to a thermal or non-thermal plasma for sterilization. Even more preferably, sterilization of the external surfaces may take place while the sterilization apparatus described herein is effecting sterilization of the instrument channel of the scoping device.

The sterilization apparatus may thus comprise a container defining a sterilization enclosure for the surgical scoping device, and a plasma generating unit for creating a non-thermal plasma or a thermal plasma within the sterilization enclosure for sterilizing an exterior surface of the surgical scoping device. The container may include separate chambers for different portions of the scoping device. For example, a first chamber may receive a control head of the surgical scoping device, and a second chamber may receive an instrument tube of the scoping device. The plasma generating unit may include an annular body for enclosing an instrument tube of the surgical scoping device. The annular body may be slidable along the instrument tube. For example, the additional apparatus may comprise a conveyor or linear treatment bed which is configured to pass the scoping device through a static sterilization apparatus which is configured to sterilize the external surfaces of the scoping device.

The withdrawal device may comprises a cable coupling element operably connected to the elongate probe at a proximal end thereof, and a motor arranged to drive the cable coupling element to cause relative movement between the elongate probe and the instrument channel in a longitudinal direction. The withdrawal device thus allows the elongate probe (or any instrument cable) to be inserted or withdrawn through an instrument channel at a predetermined rate, the predetermined rate being set by the speed of the motor. Preferably the motor is a variable speed motor such that the predetermined rate may be adjusted by a user. When used in combination with sterilization apparatus, such as described above according to the first aspect of the invention, it allows for sterilization of the instrument channel in a controlled fashion. The motor may be powered by a battery contained within the housing, or may alternatively be powered by an external power source, such as a generator used to provide energy to the distal end of the instrument cable.

The cable coupling element may be mountable in a fixed position relative to the surgical scoping device. For example, the withdrawal device may comprise a housing having an attachment portion for releasably attaching the device to a handle of the scoping device. This allows the insertion/withdrawal device and scoping device to be set up in a manner which requires minimal user interaction, for example during an instrument channel sterilization process.

The cable coupling element may comprise a plurality of rollers defining a space between them for receiving the elongate probe, the rollers being arranged to grip an exterior surface of the elongate probe whereby rotation of the rollers causes longitudinal movement of the elongate probe.

In certain embodiments, the motor is switchable between a forward mode and a reverse mode of operation, wherein the forward mode is suitable for inserting the instrument cable through the instrument channel and the reverse mode is suitable for withdrawing the instrument cable through the instrument channel. This allows the same device to be used multiple times for different purposes, though it is also envisaged that the device be disposable to ensure sterile equipment is used where needed. Providing a device which can run in both forward and reverse modes reduces costs and complications for a user, as they can simply choose which mode the device is operated in rather than buying separate insertion and withdrawal devices. Production costs are also reduced as only a single unit need be produced, suitable for each purpose.

Preferably, the device may further comprise a drum around which the instrument cable may be wound prior to insertion or during withdrawal of the instrument cable through the instrument channel. This simplifies the insertion or withdrawal procedure as the user does not need to worry about storing the instrument cable before or after use, or feeding the cable into or out of the scoping device. By winding the instrument cable about a drum, storage space and working space (e.g. during a sterilization process) may be minimized. Preferably, the drum is also contained in the housing so that the drum may provide a sterile environment for storage of the instrument cable. The drum may preferably be sized such that the bending radius of the instrument cable about the drum is sufficient to prevent damage to the cable, particularly where the instrument cable is likely to be re-used.

Preferably, the device further comprises means for disengaging the motor from the at least one roller to allow a user to freely slide the device along the instrument cable. In this way, the device can easily be slid onto or removed from the instrument cable and a user can properly position the device on the instrument cable. Disengaging the motor also allows a user to manually slide the instrument cable in an instrument channel if necessary, for example, during a sterilization process. This may be useful, for example, if there is a blockage or unexpected problem with the equipment.

Preferably, the plurality of rollers are biased towards each other. In some embodiments, the rollers may have an hourglass shape. These features ensure that there is a good fit between the rollers and the surface of the instrument cable, increasing friction to ensure that the instrument cable is smoothly pulled by the rollers and that there is no slipping of the rollers. This increases reliability of the device as well as ensuring that the speed of cable insertion/withdrawal is consistent with the speed selected or desired by the user.

In some embodiments, the motor may be a stepper motor. This may be particularly advantageous if the device is used with sterilization apparatus, as a stepper motor can be used to ensure that the instrument channel is properly sterilised at each step by waiting for a predetermined amount of time before withdrawing the instrument cable a further distance increment.

Preferably, each of the plurality of rollers is made from a plastic or silicone material. Such materials may be chosen to give a high coefficient of friction between the surface of the rollers and of the instrument cable, ensuring a complete transfer of motion from the rollers to the instrument cable. In addition, the use of a plastic or silicone material ensures that no damage is done to the instrument cable by the rollers.

The withdrawal device may be an independent aspect of the present disclosure. According to that aspect, there is provided a probe withdrawal device for moving an elongate probe through an instrument channel of a surgical scoping device, the probe withdrawal device comprising: a cable coupling element operably connected to the elongate probe at a proximal end thereof; and a motor arranged to drive the cable coupling element to cause relative movement at a predetermined rate between the elongate probe and the instrument channel in a longitudinal direction.

BRIEF DESCRIPTION OF THE DRAWINGS

Embodiments of the invention will now be described by way of example with reference to the accompanying drawings in which:

FIG. 9 is a longitudinal cross-sectional view through an integrated microwave cable assembly and plasma applicator probe tip that can be used with the present invention;

FIG. 10 is a longitudinal cross-sectional view through another coaxial plasma applicator (probe tip) that can be used with the present invention;

FIGS. 17A to 17C show a sterilization apparatus in use for sterilizing the instrument channel of a scoping device;

DETAILED DESCRIPTION; FURTHER OPTIONS AND PREFERENCES

Figure 1A:
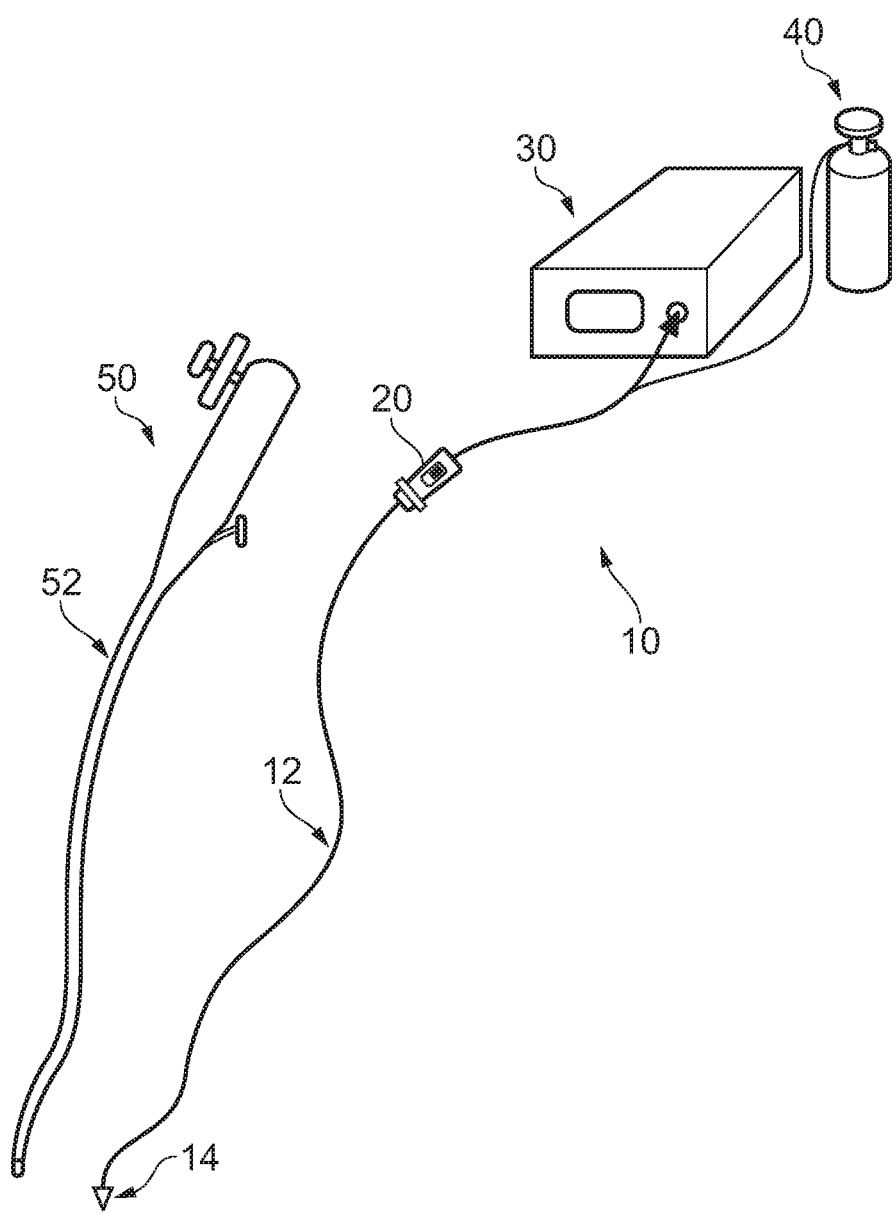
FIGS. 1A and 1B show a sterilization apparatus according to a first aspect of the invention.

FIG. 1A shows a sterilization apparatus 10 according to a first aspect of the invention. The sterilization apparatus comprises an elongate probe having a coaxial cable 12 and a probe tip 14 at its distal end. A generator 30 is connected to the coaxial cable at its proximal end. A gas supply 40 is also connected to supply gas to the probe tip 14 through a gas conduit (not shown) in the coaxial cable 12. A withdrawal device 20 is positioned on the coaxial cable 12 in order to withdraw the elongate probe from an instrument channel which runs through the insertion tube 52 of scoping device 50, in a manner which will be explained in more detail below.

Figure 1B:
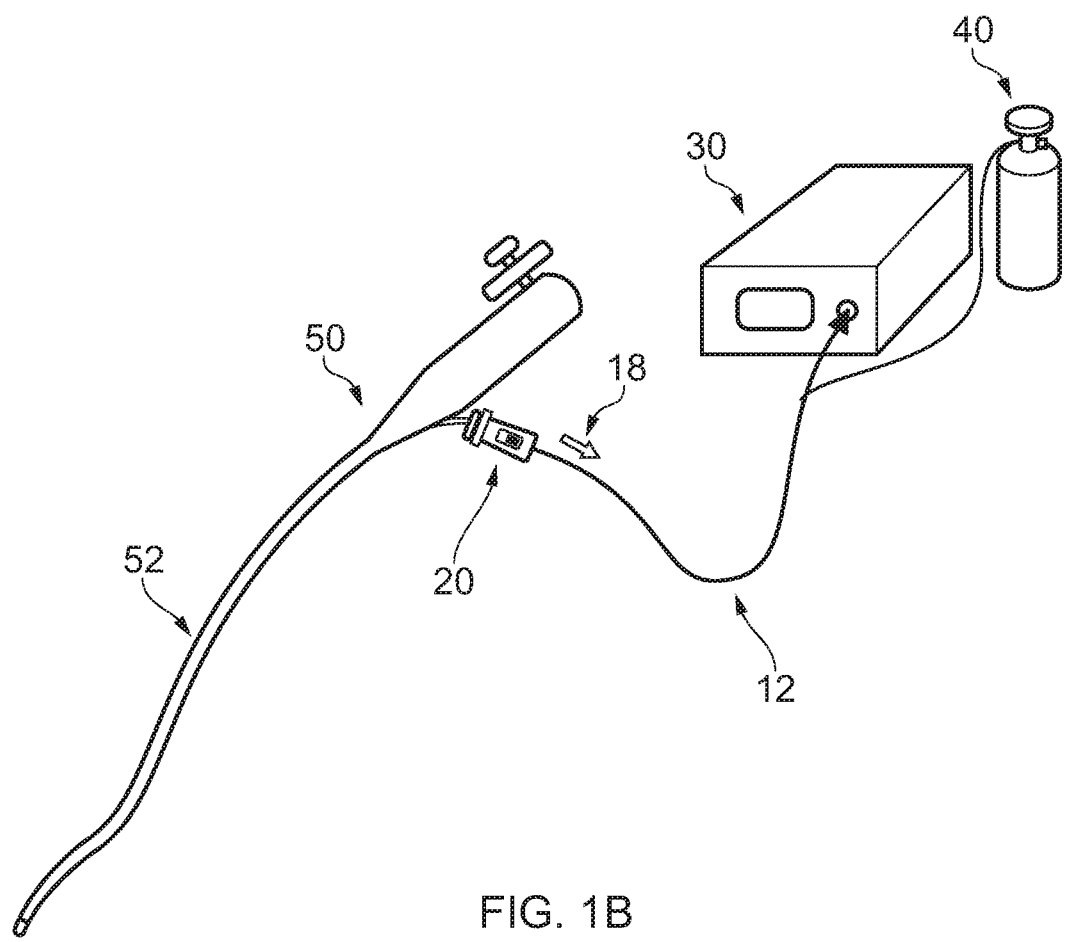

FIG. 1B shows the sterilization apparatus 10 in use. The elongate probe is within the instrument channel of the insertion tube 52, and the withdrawal device 20 is attached to the handle of the scoping device 50. The withdrawal device 20 is switched on to withdraw the coaxial cable 12 from the instrument channel of the insertion tube 52 at a predetermined rate, in a direction indicated by arrow 18. While the withdrawal device 20 is withdrawing the coaxial cable 12 and probe tip (not shown) through the instrument channel, the generator 30 is supplying RF and/or microwave frequency EM energy to the probe tip such that the probe tip is sterilizing the instrument channel. The gas supply 40 supplies gas to the probe tip through the gas conduit so that the RF and/or microwave EM energy may be used to generate a non-thermal plasma at the probe tip to destroy or eliminate micro-organisms in the instrument channel of the insertion tube 52.

Figure 2:
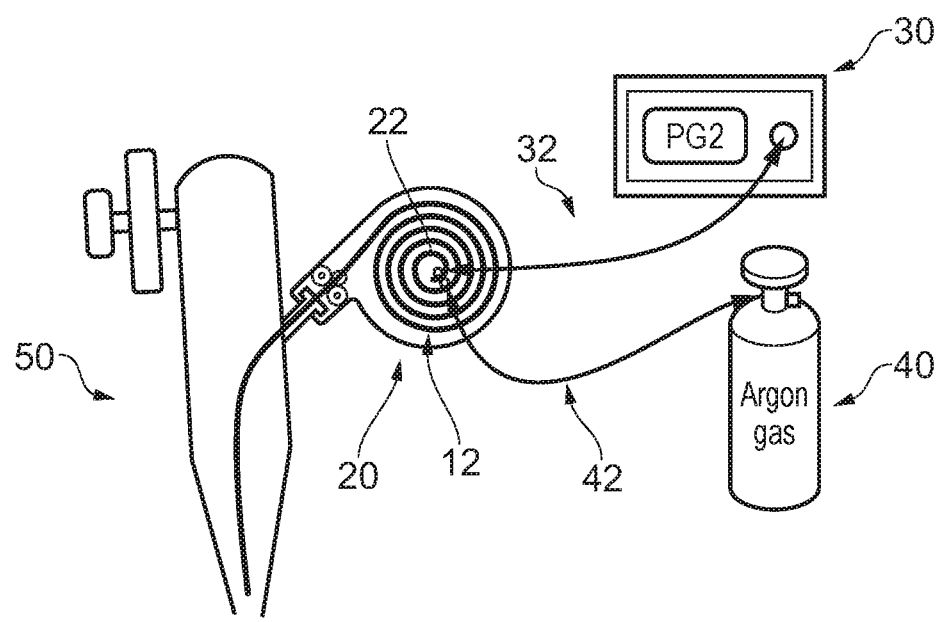
FIG. 2 shows sterilization apparatus and an alternative embodiment of a withdrawal device.

FIG. 2 shows sterilization apparatus having an alternative withdrawal device 20. In this arrangement, the withdrawal device additionally comprises a drum 22 around which the coaxial cable 12 is wrapped as it is withdrawn from the instrument channel of the scoping device 50. The generator 30 supplies RF and/or microwave EM energy to the coaxial cable 12 via a connecting wire 32 and a suitable plug on the housing of the withdrawal device 20. Similarly, gas from the gas supply 40 is conveyed to the gas conduit through a connecting tube 42. The withdrawal device 20 is discussed in more detail below.

Figure 3A:
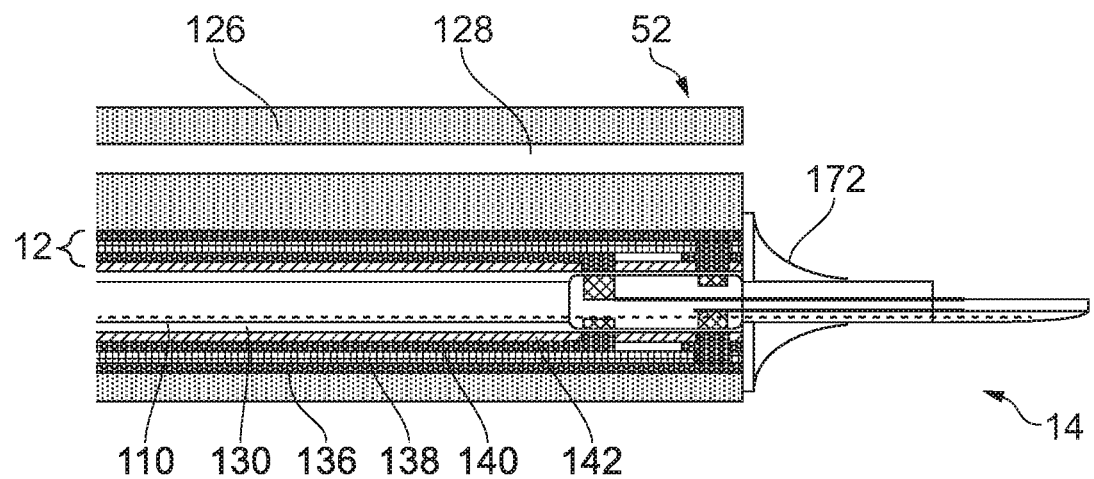
FIG. 3A is a cross-sectional view through a distal end of the elongate probe showing the probe tip and coaxial cable.

FIG. 3A is a cross-sectional view through a distal end of the elongate probe showing the probe tip 14 and a layer-structured coaxial cable 12, with a catheter 110 and probe tip 14 inserted in a channel 130 of the coaxial cable 12.

Figure 3B:
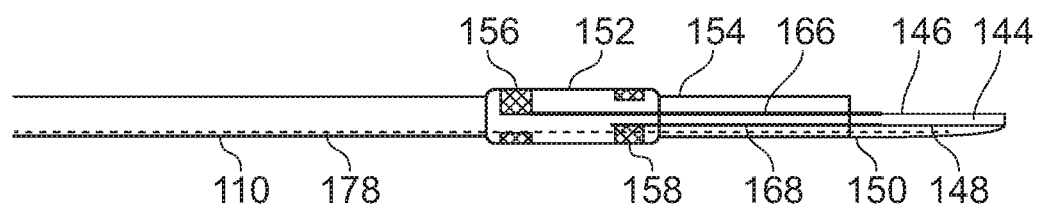
FIG. 3B shows the probe tip of FIG. 3A alone.

The probe tip 14, which is shown alone in FIG. 3B, used in sterilization of an instrument channel but may also be suitable for use in electrosurgery. In particular, the probe tip 14 shown in FIGS. 3A and 3B is configured for use as a resection instrument.

The probe tip 14 comprises a connection collar 152 attached to the distal end of the catheter 110, an extension sleeve 154 which extends distally from the connection collar 152, and a sterilization instrument connected at a distal end of the extension sleeve 154. The sterilization instrument is formed from a piece of rigid dielectric 144 that has a conductive coating (not shown) on its upper surface 146 and lower surface 148 to form two electrodes, and a smooth tapering dielectric 150 formed below the lower surface 148. The connection collar 152 comprises a short rigid cylindrical portion having a diameter selected to snugly fit in the channel 130 of the coaxial cable so that its outer surface is in physical contact with the surface that defines the channel 130 (i.e. the inner surface of wall 134). The connection collar 152 may have a larger diameter than the catheter 110. A pair of contacts 156, 158 are formed on the outer surface of the connection collar 152. The contacts 156, 158 may extend around all or part of the outer surface. In this embodiment, a back (i.e. proximal) contact 156 is arranged to electrically connect to the inner conductive layer 140 of the layer-structured coaxial cable 12, and a forward (i.e. distal) annular contact 158 is arranged to electrically connect to the outer conductive layer 136 of the layer-structured coaxial cable 12.

Figure 3C:
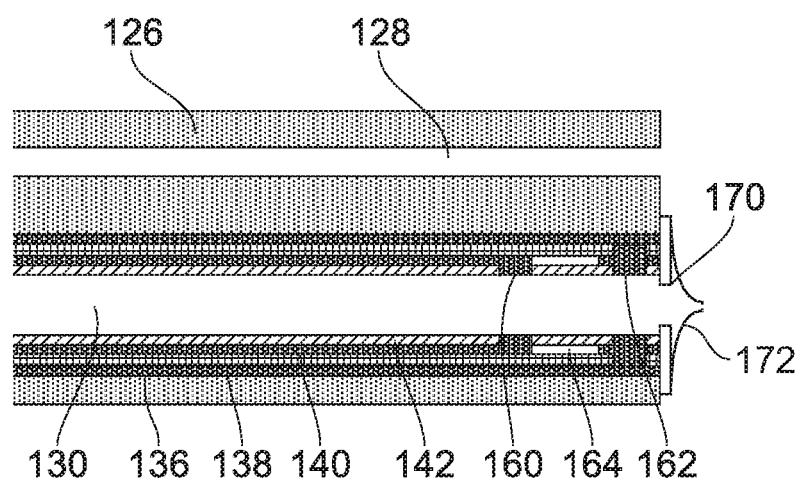
FIG. 3C shows the coaxial cable of FIG. 3A alone.

To achieve these electrical connections, the coaxial cable 12 has a pair of longitudinally spaced terminals 160, 162 that protrude through the innermost layer 142 at the distal end of the channel 130, as shown in FIG. 3C. The terminals 160, 162 may extend around all or part of the inner surface of the channel 130. In this embodiment, a back (i.e. proximal) terminal 160 extends through the innermost layer 142 from a distal end of the inner conductive layer 140, and a forward (i.e. distal) terminal 162 extends through both the dielectric layer 138 and the innermost layer 142 from a distal end of the outer conductive layer 136. The outer conductive layer 136 extends longitudinally beyond a distal end of the inner conductive layer 140. The inner conductive layer 140 thus terminates at the back terminal 160, i.e. there is a gap 164 (e.g. an air gap or other insulating material) located beyond of the distal end of the inner conductive layer 140 before the forward terminal 162.

A conductive rod 166 extends from the back contact 156 through the extension sleeve 154 to provide an electrical connection for the conductive coating on the upper surface 146 of the piece of rigid dielectric 144. The upper surface 146 is therefore electrically connected to the inner conductive layer 140 of the coaxial cable 14. Similarly, a conductive rod 168 extends from the forward contact 158 through the extension sleeve 154 to provide an electrical connection for the conductive coating on the lower surface 148 of the piece of rigid dielectric 144. The lower surface 148 is therefore electrically connected to the outer conductive layer 136 of coaxial cable 12.

The extension sleeve 154 may be a rigid tube of dielectric material for both protecting and electrically insulating the conductive rods 166, 168. The extension sleeve 154 may have an electric length that corresponds to half a wavelength of the microwave energy that is conveyed by the extension sleeve 154. The conductive rods 166, 168 may be separately enclosed (e.g. coated of otherwise covered) by dielectric, e.g. glue, plastic or some other insulator, to prevent breakdown, especially where they are close together.

A distal end of the connection collar 152 may abut against a stop flange 170 formed at the distal end of the channel 130. The probe tip 14 can therefore be secured in place with an electrical connection between the contacts 156, 158 and terminals 160, 162, e.g. by maintaining a pushing force on the catheter 110. Although in this embodiment the connection collar 152 performs a dual function of electrical connection and physical stop, it is possible for these functions to be performed by separate features, in which case the connection collar 152 may be located further back in the channel 130 and the extension sleeve 154 may be longer.

To prevent material escaping backwards into the channel, a seal 172 may be formed over the entrance to the channel 130.

The catheter 110 may be a hollow tube for conveying a gas conduit or control lines 178 to the probe tip 14. In this embodiment, the gas conduit extends right through to the distal end of the probe tip for delivering argon or another gas for plasma sterilization. The gas conduit 178 may also be adapted to deliver fluid such as saline to the probe tip 14 for performing electrosurgery.

Figure 4:
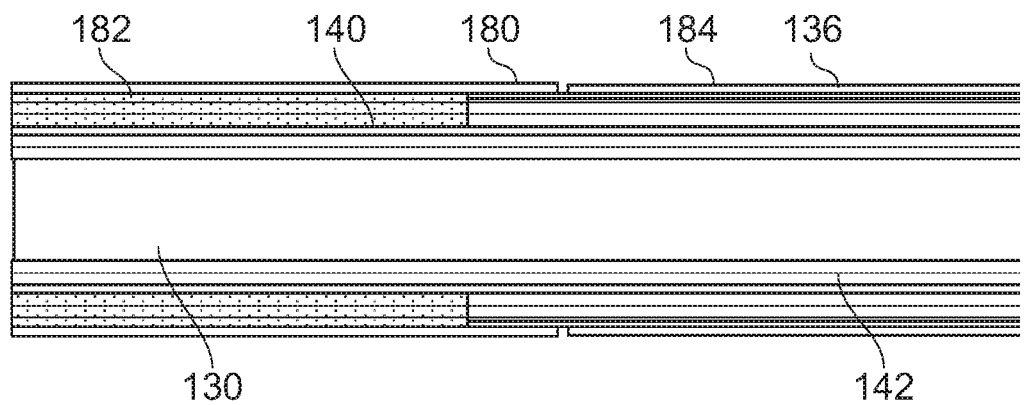
FIG. 4 is a cross-sectional view through an alternative probe tip embodiment.

FIG. 4 shows another embodiment of a probe tip 14 which can be used with the layer-structured coaxial cable 12 described above with respect to FIGS. 3A-3C. The probe tip 14 comprises an extension of the innermost layer 142 and inner conductive layer 140. In this embodiment, the innermost layer 142 is a PTFE tube. The inner conductive layer acts as a first electrode of the probe tip 14. The probe tip 14 also comprises a dielectric material 182 which is placed over the first electrode 140, and a second electrode 180 over the dielectric material 182. The dielectric 182 is a MACOR cylinder and the second electrode 180 is formed of a thin wall copper tube. The second electrode 180 is electrically connected to the outer conductive layer 136, which extends beyond the distal end of a sleeve 184 covering the coaxial cable 12. Gas may be supplied to the distal end of the probe tip 14 through the channel 130, which extends through the elongate instrument to its proximal end where gas may be supplied e.g. from a gas canister. The probe tip 14 has an outer diameter of 2.5 mm, the dielectric layer 182 has a wall thickness of 0.325 mm, and the channel 130 a diameter of 1 mm.

Figure 5:
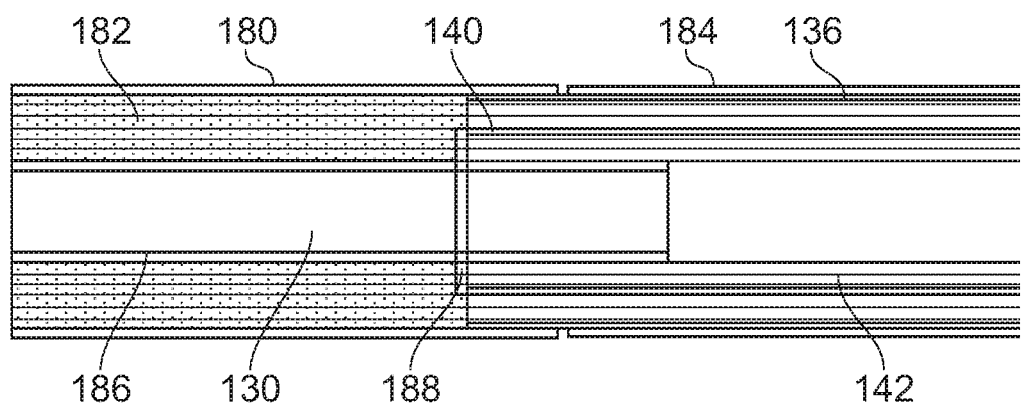
FIG. 5 is a cross-sectional view through another alternative probe tip arrangement.

FIG. 5 shows an alternative probe tip 14 which can be used with the layer-structured coaxial cable 12 described above with respect to FIGS. 3A-3C. The probe tip 14 comprises a first electrode 186 which is a tube structure inserted into the innermost layer 142, and which defines part of the channel 130. The innermost layer 142 may be a PTFE tube. Dielectric layer 182 is provided over the first electrode 186. Similar to the embodiment shown in FIG. 4, the second conductor 180 is a thin wall copper cylinder connected to the outer conductive layer 136. The first electrode 186 is connected to the inner conductive layer 140 via a metal ring 188 which is gripped between the dielectric material 182 and the innermost layer 142. The outer diameter of the probe tip 14 is 2.5 mm, the channel 130 has a diameter of 0.8 mm and the dielectric 182 has a wall thickness of 0.65 mm. The reduced channel 130 diameter and increased dielectric 182 thickness increases the impedance of the probe tip 14, allowing a lower dielectric constant material to be used for the dielectric layer 182.

Other probe tip embodiments discussed herein may also be used with a 'conventional' coaxial cable; i.e. a coaxial cable not having the layered structure described above.

Figure 6:
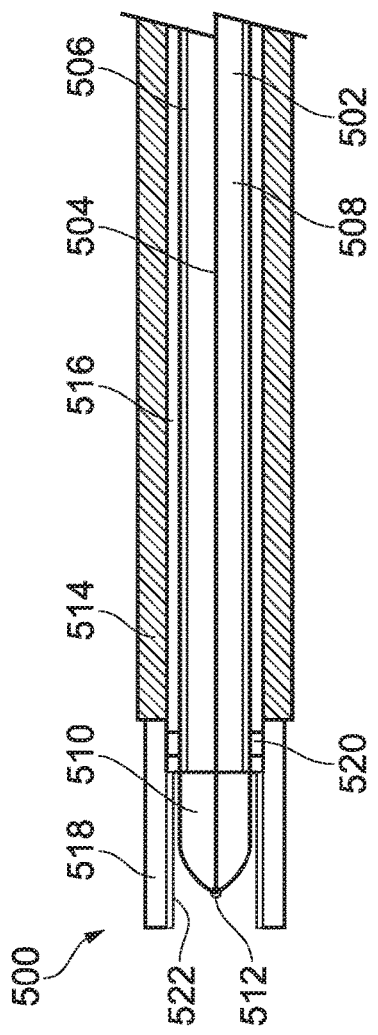
FIG. 6 is a cross-sectional view through yet another embodiment of a probe tip.

FIG. 6 shows a cross-sectional view through a probe tip which is suitable for generating plasma at the distal end of an elongate instrument. The tip shown may also be used as an electrosurgical instrument. The elongate instrument 500 is cylindrical, and sized to fit down the instrument channel of a scoping device, e.g. an endoscope. The instrument comprises a coaxial cable 502 having an inner conductor 504 and an outer conductor 506 separated from the inner conductor 504 by a dielectric material 508. The outer conductor 506 is exposed around at the outside surface of the coaxial cable 502. At the distal end of the coaxial cable 502, the inner conductor 504 extends beyond the outer conductor 506 and is surrounding by a dielectric cap 510, e.g. made of PEEK or the like. The cap 510 is a cylinder having substantially the same diameter as the coaxial cable 502. The distal end of the cap 510 forms a rounded, e.g. hemispherical dome. The inner conductor 504 terminates at its distal end at a rounded tip 512 which projects beyond the end of the cap 510. The coaxial cable 502 is mounted within a sleeve 514, which preferably includes internal braids (not shown) to impart strength. The sleeve is dimensioned to fit within the instrument channel of a scoping device. There is an annular gap 516 between the inner surface of the sleeve 514 and the outer surface of the coaxial cable 502 (i.e. the exposed outer conductor) which forms a gas conduit for conveying gas introduced at the proximal end of the sleeve 514 to the distal end. A conductive terminal tube 518 is mounted at the distal end of the sleeve 514. For example, the conductive terminal tube 518 may be welded to the sleeve 514.

In the configuration shown in FIG. 6, the rounded tip 512 of the inner conductor 504 forms a first electrode and the conductive terminal tube 518 forms a second electrode. An electric field for striking a plasma in the gas flowing from the annular gap 516 is formed between the first electrode and second electrode by applying suitable energy (e.g. RF and/or microwave frequency energy) to the coaxial cable. The conductive terminal tube 518 is electrically connected to the outer conductor 506 of the coaxial cable 502 by a plurality of radially projecting bumps 520 on the inner surface of the conductive terminal tube 518. There may be two, three, four or more bumps 520 spaced from one another around the inner circumference of the conductive terminal tube 518. Spacing the bumps in this manner permits gas to flow past. An insulating liner 522 is mounted around the inside surface of the conductive terminal tube 518 along a distal length thereof. The insulating liner 522 may be made of polyimide or the like. The purpose of the liner 522 is to provide a suitable dielectric barrier between the first electrode and second electrode to ensure that the applied RF and/or microwave frequency energy results in an electric field with high voltage for striking the plasma. There is a small gap between the liner 522 and the cap 510 to permit gas to flow past.

Figure 7:
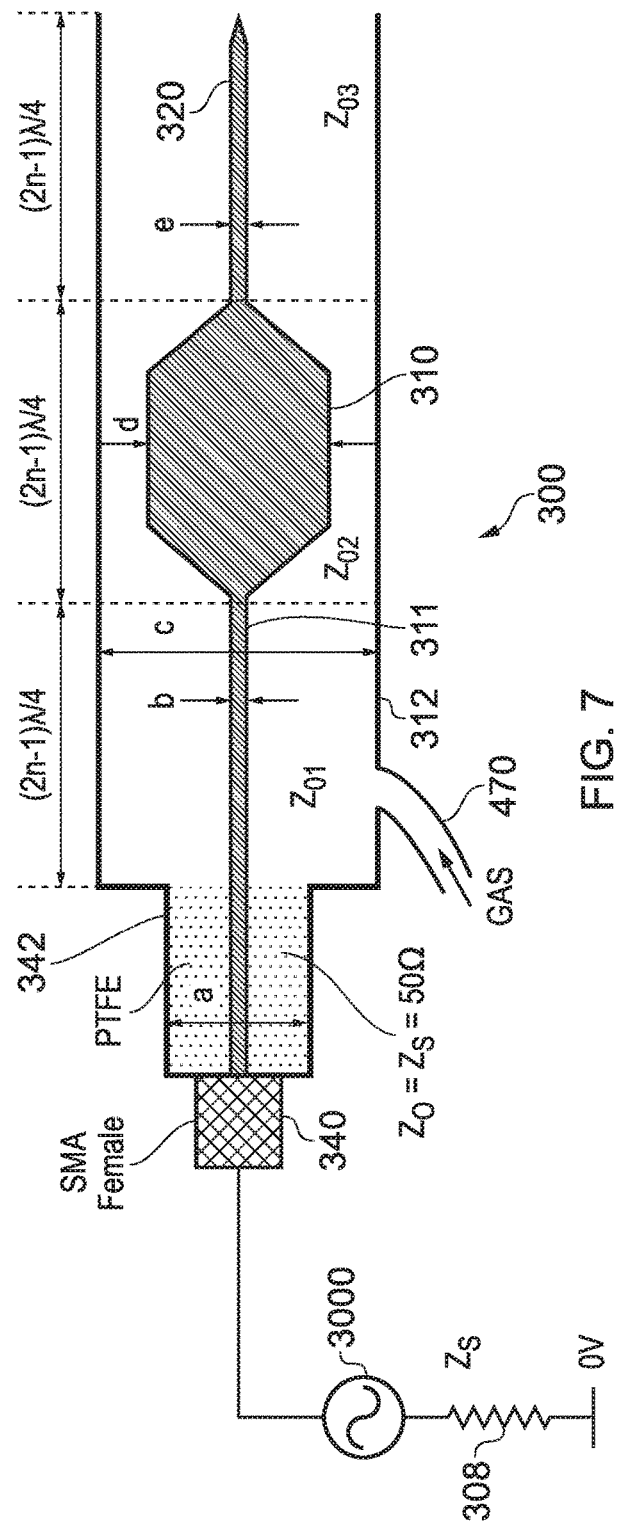
FIG. 7 is a longitudinal cross-sectional view through a coaxial plasma applicator (probe tip) that can be used with the present invention.

FIG. 7 is a longitudinal cross-sectional view through a coaxial plasma applicator (probe tip) that can be used in the present invention. The plasma sterilization apparatus need not be limited to use with this type of structure. Indeed this example is provided to explain the theory behind the use of voltage transformers (or impedance transformers) in the generation of plasma in the applicator. In fact it may be possible to generate the plasma without voltage transformers, especially if an impedance adjustor is present. The plasma applicator 300 shown in FIG. 7 is a coaxial structure comprising three quarter wave impedance transformers, where the diameter of the center conductor is changed to produce three sections with different characteristic impedances. The impedances are chosen such that the voltage at the distal end of the structure is much higher than the voltage at the proximal (generator) end of the structure.

If the physical length of each section is equal to an odd multiple of the quarter electrical wavelength, i.e.

$$L = \frac{(2n-1)\lambda}{4},$$

where L is length in meters, n is an integer, and $\lambda$ is wavelength at frequency of interest in meters, then the following equation applies $$Z_0 = \sqrt{Z_L Z_S},$$

where $Z_0$ is the characteristic impedance of the coaxial line in ohms, $Z_L$ is the load impedance seen at the distal end of the section in ohms, and $Z_S$ is the source impedance seen at the proximal end of the section in ohms. By algebraic manipulation of this equation, the load impedance can be expressed as $$Z_L = \frac{Z_0^2}{Z_S}.$$

It can therefore be seen that if the characteristic impedance of the transformer section is high and the source impedance is low then the load impedance can be transformed to a very high value. Since the power level at the generator end of the antenna should theoretically be the same as that at the load end, the following can be stated $$P_{in} = P_{out} \Rightarrow P_{in} = \frac{V_L^2}{Z_L},$$

which means the voltage at the distal end can be expressed as $V_L = \sqrt{P_{in} Z_L}$. Thus it can be seen that if $Z_L$ can be made as large as possible then the value of the voltage at the distal end of the antenna structure $V_L$ will also be very large, which implies that the electric field will also be high. Since it is required to set up a high electric field in order to strike the plasma, it may be seen that this structure can be used to set-up the correct conditions to strike the plasma.

Considering the structure shown in FIG. 7, the microwave generator 3000 is indicated schematically as having a source impedance ($Z_S$) 308. The power from the generator 3000 enters the applicator 300 via a coaxial cable (not shown) using microwave connector 340. Connector 340 may be any microwave connector that is capable of operating at the preferred frequency of operation and can handle the power level available at the output of power generator 3000, e.g. N-type or SMA type connectors may be used. Microwave connector 340 is used to launch the microwave power into the plasma generating region, which includes an antenna structure described below.

The first stage of the antenna structure is a 50Ω coaxial section that consists of a center inner conductor (a first electrode) with an outside diameter b and an outer conductor (a second electrode) with an inside diameter a. The space between the inner and outer conductors contained within the first section is filled with a dielectric material 342, which is labelled here as PTFE. The characteristic impedance of the first section of the antenna is shown here to be the same as that of the generator, i.e. 50Ω, and can be described as follows $$Z_0 = Z_S = \frac{138}{\sqrt{\varepsilon_r}} \log_{10} \frac{a}{b} = 50 \ \Omega,$$

where $\varepsilon_r$ is the relative permittivity of the filler material, $Z_0$ is the characteristic impedance of the first section and $Z_S$ is the source impedance (or the generator impedance). The second section is the first quarter wave impedance transformer 311 whose characteristic impedance $Z_{01}$ is higher than that of the first section and can be calculated using $$Z_{01} = 138 \log_{10} \frac{c}{b},$$

where c is the inside diameter of the outer conductor 312. Since the second section is filled with air (or at least the gas from gas feed 470), the relative permittivity $\varepsilon_r$ is equal to unity and so the square root term disappears from the equation that describes the impedance of a coaxial transmission line. A practical example of the impedance of the second section may be b=1.63 mm and c=13.4 mm. With such dimensions, $Z_{01}$ would be 126.258Ω.

The third section is the second quarter wave impedance transformer 310, whose characteristic impedance $Z_{02}$ is lower than that of the first section and second sections, and can be calculated using $$Z_{02} = 138 \log_{10} \frac{c}{d},$$

where d is the outer diameter of the inner conductor. It is desirable to taper the input and output ends of the center conductor in order to make the step from the high impedance condition to the low impedance condition more gradual in order to minimize mismatches occurring at the junctions between the two impedances. A suitable angle for the taper is 45°. A practical example of the impedance for the third section may be d=7.89 mm and c=13.4 mm. With such dimensions, $Z_{02}$ would be 31.744Ω.

The fourth section is the final section and consists of a third quarter wave impedance transformer 320, whose characteristic impedance $Z_{03}$ is higher than that of the third section, and can be calculated using $$Z_{03} = 138 \log_{10} \frac{c}{e},$$

where e is the outer diameter of the inner conductor. It is desirable for the distal end of the inner conductor to be sharp and pointed in order to maximize the magnitude of the electric field produced at this point. A practical example of the characteristic impedance for the fourth section may be e=1.06 mm and c=13.4 mm. With such dimensions, $Z_{03}$ would be 152.048Ω.

For the arrangement using three quarter wave transformers as shown in FIG. 7, the load impedance $Z_L$ seen at the distal end of the antenna may be expressed as $$Z_L = \frac{Z_{03}^2 Z_{01}^2}{Z_{02}^2 Z_S}.$$

Using the values of characteristic impedance calculated above for the three transformers, $Z_L$ would be 7,314.5Ω. If the input power is 300 W, then the voltage at the output will be $V_L = \sqrt{P_{in} Z_L} = 1481.33$V. The electric field generated at the end of this structure will thus be $$E = \frac{2V_L}{c} = 221094.03 Vm^{-1}.$$

This large electric field may enable the plasma to be set up using any one of a number of gases and gas mixtures.

The inner conductor may be a single conductor whose diameter changes from b to d to e from the proximal end to the distal end. The outer conductor has the same inner diameter c for the length of the three impedance transformer sections and is reduced to a at the first section. The material used for the inner and outer conductors may be any material or composite that has a high value of conductivity, for example, copper, brass, aluminum, or silver coated stainless steel may be used.

The gas or mixture of gases is fed into the structure via gas conduit 470 and the gas fills the interior (the plasma generating region) of the plasma applicator. The applicator is dimensioned to fit within the instrument channel of a scoping device.

Figure 8:
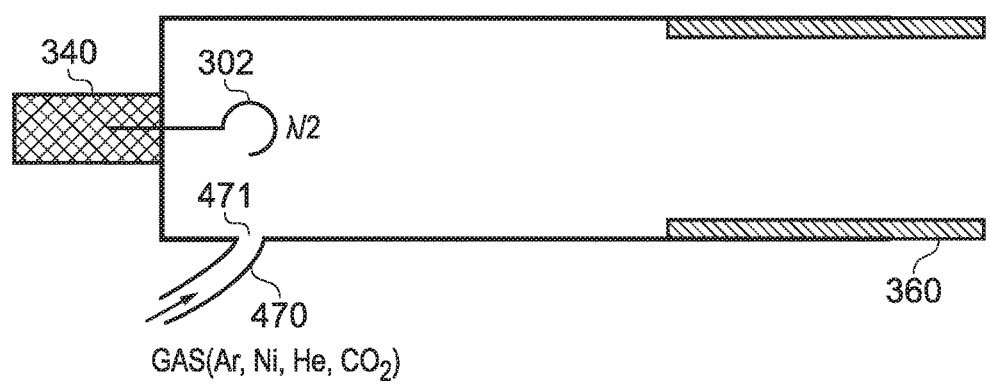
FIG. 8 is a longitudinal cross-sectional view through a waveguide plasma applicator (probe tip) that can be used with the present invention.

FIG. 8 shows a plasma applicator probe tip 300 in which a waveguide cavity is used to create the field to generate the plasma. In this particular embodiment, an H-field loop 302 is used to transfer the microwave energy from the microwave generator into the waveguide antenna, and the gas mixture is introduced into the structure via gas feed 471, which is connected to gas conduit 470. It may be preferable for H-field loop to have a physical length that is equal to half the wavelength at the frequency of interest or operation, and for the distal end of said loop to be connected to the inside wall of outer conductor. The connection may be made using a weld or solder joint. The H-field loop may be considered a first electrode and the waveguide antenna a second electrode.

Although not illustrated in FIG. 8, impedance transformers may also be introduced into the waveguide embodiment to generate high electric fields at the distal end of the applicator. In other words, the waveguide antenna may comprise of a plurality of sections that have a length equal to an odd multiple of the quarter loaded or unloaded wavelength at the frequency of interest, i.e.

$$L = \frac{(2n-1)\lambda}{4}.$$

In order to reduce the dimensions of the waveguide (length, width, or diameter) the waveguide may be filled with a dielectric, or magnetic, or composite material where the wavelength is reduced by a function of the inverse of the square root of the relative permittivity, or the relative permittivity, or the product of the two. A number of impedance transformers may be introduced by loading one or a plurality of the sections that form the transformer. In the instance whereby the waveguide structure is loaded with a dielectric or magnetic material (or combination of the two), it may be preferable for the loading material to be porous or have a plurality of holes drilled into it to enable the gas or gas mixture to flow inside the waveguide sections.

In order to change the impedance of the waveguide to produce the desired quarter wavelength transformations within the structure, it is necessary to make adjustments to the geometry of the structure or change the loading material. For a rectangular waveguide, the characteristic impedance of the waveguide cavity may be expressed as $$Z_0 = 377 \frac{b}{a} \sqrt{\frac{\mu_r}{\varepsilon_r} \frac{\lambda_g}{\lambda}},$$

where $$\frac{\lambda_g}{\lambda}$$

is $$\frac{1}{\sqrt{1 - f_{c/2f}}},$$

b is the height of the guide (or the length of the short wall), a is the width of the guide (or the length of the long wall), $\mu_r$ is the relative permeability of the magnetic loading material, $\varepsilon_r$ is the relative permittivity of the dielectric loading material, $f_c$ is the cut off frequency of the guide, and f is the frequency of operation.

In FIG. 8, an additional material 360 is added at the distal end of the waveguide. The additional material 360 may be a quartz tube used to increase the electric field at the distal end of the antenna structure.

FIG. 9 provides a detailed diagram of a probe tip comprising an integrated microwave cable assembly and plasma applicator. In this arrangement, the integrated gas and microwave cable assembly comprises a coaxial arrangement formed using two tubes. The first tube 314 is a relatively thick walled tube made from a flexible dielectric material and is coated with a layer of metal (e.g. a metallization layer of high conductivity, e.g. made from silver, copper or gold) on both the inner and outer walls 318, 319 thereof. The second tube 313 is a relatively thin walled tube made from a flexible material. The first tube 314 is suspended inside the second tube 313 using spacers 312 that may be made from a metallic or dielectric material and must allow gas to flow within and along the channel formed between the outer wall 318 of first tube and the inner wall of second tube 313. The plasma applicator comprises two impedance transformers 310, 320, a gas conduit 315 from center channel of first tube 314 into the applicator, and a gas extraction passage 316 from the applicator along a channel formed between the outer wall of first tube and the inner wall of second tube. A first section 321 of the inner channel used to feed gas into the applicator is solid to enable the center pin within microwave connector 340 to be electrically connected to the new microwave cable assembly. The input microwave connector may be any connector suitable for carrying microwave power up to 600 W CW at the frequency of interest, e.g. SMA or N-type connectors may be used. Microwave power is delivered to the connector 340 from a generator.

The center 311 of the inner conductor 319 used to form the coaxial microwave cable assembly is hollow due to the fact that the microwave field produced at the frequency of interest only requires a small amount of wall thickness to enable the field to efficiently propagate along the cable or waveguide, thus the center portion 311 of inner conductor 319 may be transparent to the microwave field. Similar criteria apply to the thickness of the outer conductor 318, i.e. it is only a thin layer 318 on the outer surface of the first tube 314 that plays an important part in the microwave field or wave propagation along the wave guiding channel. The first tube 314 should preferably be made from a low loss dielectric material, e.g. low density PTFE, in order to ensure that the power loss along the structure (the insertion loss) is minimized. The integrated applicator or antenna is formed inside second tube 313 and forms an integral part of the cable assembly, aiding insertion of the device through an instrument channel, e.g. of an endoscope. The plasma applicator shown in FIG. 9 consists of two quarter wave impedance transformer sections 310, 320. The first section is a low impedance section whose impedance is determined by the ratio of the diameter of inner conductor (g) and the diameter of outer conductor (i) as described above. The outer conductor may be an extension of outer conductor 318 within the integrated microwave cable assembly used to transport the microwave energy from the generator to the applicator. The gas from within channel 311 is fed into the applicator through a hole, groove, or channel made in inner conductor 311. The second transformer section is a high impedance section whose impedance is determined by the ratio of the diameter of inner conductor (h) and the diameter of outer conductor (I). The material used to form inner conductor may be a material that is able to withstand high temperature without change of physical form or characteristic, e.g. tungsten.

A quartz tube 319 is located at the distal end of the applicator between the inner and outer conductors. The quartz tube reduces the likelihood of arcing and promotes plasma striking in the plasma generating region. Here the plasma plume 1000 is directed out of the open end of the applicator by the flow of gas from the center channel 311. An annular gap between the quartz tube and outer conductor leads to the outer channel 316. This channel may be connected to a pump for extracting excess or residual gas from the sterilization site.

Figure 11:
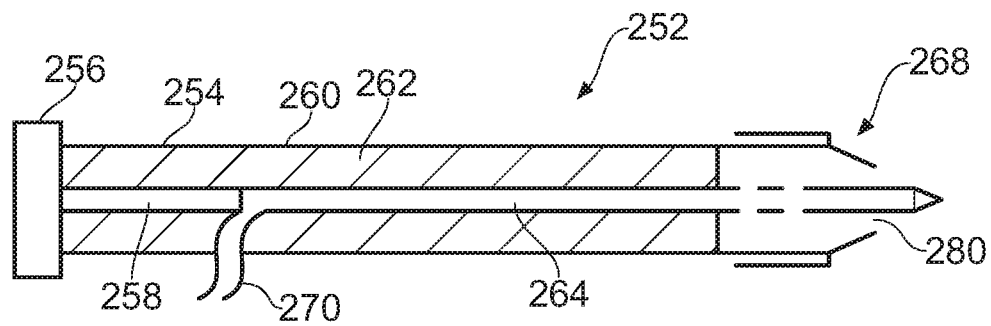
FIG. 11 is a longitudinal cross-sectional view through another coaxial plasma applicator (probe tip) that can be used with the present invention.

FIGS. 10 and 11 show two elongate instrument structures 250, 252 that, in addition to performing sterilization of an instrument channel, may be used to cut, coagulate, ablate and sterilize biological tissue. The overall diameter of these structures may range from less than 1 mm to greater than 5 mm. In both cases, the instrument structures 250, 252 comprise a coaxial cable 254 having a connector 256 at a proximal end to receive microwave frequency energy and RF energy from a generator (not shown). The coaxial cable 254 has an inner conductor 258 separated from and coaxial with an outer conductor 260 by a suitably low loss dielectric material 262, which may be low density PTFE, a microporous material such as Gortex® or the like.

In this embodiment, a distal portion of the inner conductor 258 is hollowed out to form a conduit 264 extending toward the instrument tip 266, 268. It is possible to make inner conductor 258 hollow by making use of the skin effect in conductors that occurs at microwave frequencies.

When a conductive material is exposed to an EM field, it is subjected to a current density caused by moving charges. Good conductors, such as gold, silver and copper, are those in which the density of free charges are negligible and the conduction current is proportional to the electric field through the conductivity, and the displacement current is negligible with respect to the conduction current. The propagation of an EM field inside such a conductor is governed by the diffusion equation, to which Maxwell's equations reduce in this case. Solving the diffusion equation, which is valid mainly for good conductors, where the conduction current is large with respect to the displacement current, it can be seen that the amplitude of the fields decay exponentially inside the material, where the decay parameter (δ) is described using the following equation:

$$\delta = \frac{1}{\sqrt{\frac{\omega\mu\sigma}{2}}},$$

wherein δ is known as the skin depth and is equal to the distance within the material at which the field is reduced to 1/e (approximately 37%) of the value it has at the interface, σ is the conductivity of the material, μ is the permeability of the material, and ω is the radian frequency or $2\pi f$ (where f is the frequency). From this, it can be seen that the skin depth decreases when the frequency of the microwave energy increases as it is inversely proportional to the square root of this frequency. It also decreases when the conductivity increases, i.e. the skin depth is smaller in a good conductor than it is in another less conductive material.

For the microwave frequencies of interest and the materials of interest for implementing the structures shown in FIGS. 10 and 11, the skin depth is around 1 μm, hence the inner conductor/first electrode 258 used in the construction of the instruments described here require a wall thicknesses of only about 5 μm to enable most of the microwave field to propagate. This implies that a hollow center conductor can be used without causing any change to the EM wave propagating along the structure.

A fluid feed inlet 270 is formed through the side of the coaxial feed cable 254 to permit an external fluid (gas and/or liquid) supply to communicate with the conduit 264 to deliver fluid to the probe tip 266, 268. Preferably, the fluid feed does not affect the electromagnetic field that has been set up in the co-axial transmission line structure. EM modelling is performed to determine optimal feed points where the EM field is unaffected.

FIG. 10 is a longitudinal cross-sectional view through a probe tip for delivering plasma, wherein the probe tip has a coaxial structure. In FIG. 10, the probe tip 266 includes an outlet 272 from the conduit, which permits the gas to enter the interior of the probe tip 266 in which the dielectric material 262 is removed, which may form a plasma generation region 274. In this particular arrangement, the outlet 272 comprises a plurality of slots on the inner conductor/first electrode 258 within the plasma generation region 274. In the plasma generation region 274, the electric field set up by the microwave frequency EM energy and/or RF field ionizes the gas to produce plasma in the same region. The plasma may be thermal or non-thermal and may be used to sterilize the instrument channel of a scoping device, sterilize tissue, provide a local return path for the RF current, produce surface coagulation and/or assist with tissue cutting. The plasma may be formed in the cavity by initially using energy at the RF frequency to provide the voltage necessary to strike the plasma and then using energy at the microwave frequency to enable the plasma to be sustained. Where the distance between the outer surface of the inner conductor and the inner surface of the outer conductor is very small, i.e. less than 1 mm, the microwave field may be used to strike and maintain plasma. Similarly, it may only be necessary to use the RF field to produce both non-thermal plasma for sterilization and thermal plasma for surface ablation and/or tissue cutting.

The distal end 276 of the inner conductor/first electrode 258 in the probe tip 266 is a solid pointed section, which may take the form of a sharp needle with a small diameter, i.e. 0.5 mm or less, which may be particularly effective when performing tissue cutting. The distal end 277 of the plasma generation region 274 is open to permit plasma to be delivered out of the elongate instrument.

A quarter wave (or odd multiple thereof) balun 278, comprising a third coaxial conductor that is shorted at its distal end and open at its proximal end is connected to the structure to prevent microwave currents from flowing back along the outer conductor 260 to the coaxial cable 254, which can cause the profile of the microwave energy to become non-optimal.

The composition of gas and its flow rate and delivery profile, together with the power level and profile of the supplied RF EM energy and/or microwave EM energy determines the type of plasma that is set up in plasma generation region 274 of the elongate instrument.

FIG. 11 is a longitudinal cross-sectional view through another coaxial plasma applicator. The elongate instrument 252 in FIG. 11 has a similar probe tip structure to the instrument shown in FIG. 10 except that outer conductor/second electrode 260 has been continued such that it ends closer to the distal end 276 of the inner conductor/first electrode 258 in the probe tip 268. Here the outer conductor 260 takes the form of a pointed cone at the distal end of the probe tip 268. The slope of outer conductor/second electrode may be at the same angle as the slope of the solid pointed section. A jet of plasma may be emitted through a small gap 280 that separates the inner conductor 258 from the outer conductor 260 in this region.

The probe tip may be arranged such that the initial ionization discharge or breakdown of the gas occurs between the distal end of the outer conductor 260 and the solid pointed section of the inner conductor 258. The solid pointed section may be cone shaped, which is a preferred structure for use as a surgical instrument.

Figure 12:
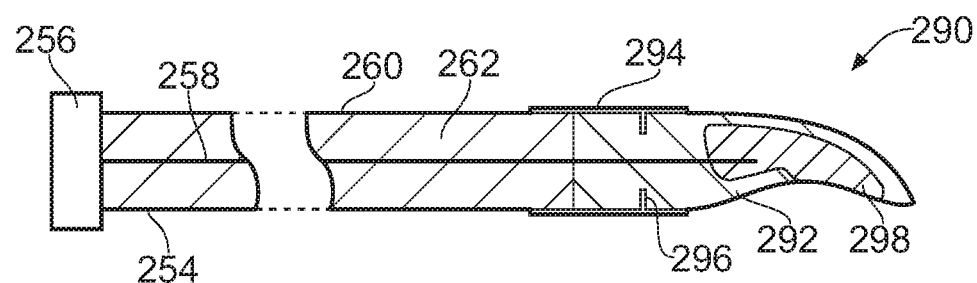
FIG. 12 is a longitudinal cross-sectional view through another elongate instrument 290 that can be used with the present invention.

FIG. 12 depicts an elongate instrument 290 suitable for use in the present invention. The probe tip shown is suited for gastrointestinal procedures in addition to instrument channel sterilization. The elongate instrument 290 comprises a coaxial cable 254 having an inner conductor 258 separated from and coaxial with an outer conductor 260 by a dielectric material 262. A probe tip 292 is connected at the distal end of the coaxial cable 254. A connector 256 is connected to the proximal end of the coaxial cable to receive RF EM energy and microwave frequency EM energy from a generator.

The probe tip 292 is a unitary piece of dielectric material (e.g. low loss Dynallox® Alumina) having two separate layers of metallization formed thereon to form first and second electrodes. The inner conductor 258 of the coaxial cable 254 extends beyond the distal end of the coaxial cable 254 into the interior of the probe tip 292. From there it is electrically connected to one of the layers of metallization. The outer conductor 260 of the coaxial cable 254 is connected to the other layer of metallization. The probe tip 292 is fixed to the coaxial cable 254 by a sleeve 294 (e.g. of stainless steel), which may be crimped to force securing tabs 296 into corresponding notches in the ceramic body of the probe tip 292. The length of the sleeve 294 may be selected to match the impedance of the probe tip 292 to the coaxial cable 254, i.e. it may act as a tuning stub.

The layers of metallization are provided on the side surfaces of the probe tip 292. The layers are separated from each other by the ceramic so that it effectively forms a planar transmission line. In this embodiment, the layers of metallization are set back from the side edges and the distal edge of the probe tip except at regions where it is desired to emit an RF EM field. FIG. 12 shows schematically a first layer of metallization 298 which is set back slightly from the edges of the probe tip except along a region along the bottom edge.

In this embodiment, the probe tip 292 has a hooked shape where one of the edges of the probe tip 292 curves inwards and outwards, i.e. defines a recess. The recess may include a substantially proximally facing surface for facilitating tissue removal, e.g. by permitting tissue to be pulled, scooped or scraped away from the treatment site. The region along the bottom edge (the RF cutting region) to which the first layer of metallization 298 extends is on the inside of the recess.

The length of the probe tip 292 that extends from the sleeve 294 to deliver RF and microwave energy may be between 3 mm and 8 mm, preferably 4 mm. The width of the probe tip may be similar to the diameter of the coaxial cable, e.g. between 1.1 mm and 1.8 mm, preferably 1.2 mm. The thickness of the distal part of the probe tip 292 may be between 0.2 mm and 0.5 mm, preferably 0.3 mm.

The general shape of the distal end of the instrument is of a spoon or scoop having a radius commensurate with that of the inner region of the vessel (e.g. bowel) in which treatment is to take place. For example, the curved arrangement shown may be suitable for getting underneath a polyp and scooping it out.

The instrument may incorporate a gas conduit (not shown) to provide a gas supply to the probe tip for production of thermal or non-thermal plasma. The conduit may also supply liquid (e.g. saline) for injection capability during use as an electrosurgical instrument.

For example, the gas and/or saline could be introduced along the inner conductor of the coaxial feed line in a manner similar to the embodiments shown in FIGS. 10 and 11, to be injectable out of an aperture formed in the probe tip 292. Alternatively a separate gas conduit may be mounted alongside the coaxial feed line.

Figure 13:
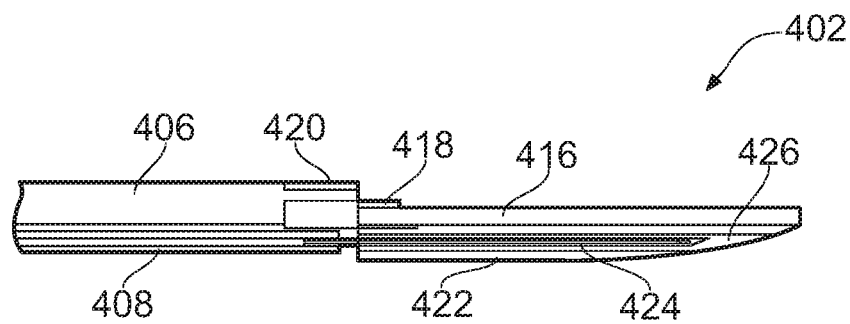
FIG. 13 is a longitudinal cross-sectional view through another probe tip that can be used with the present invention.

An alternative embodiment of a probe tip which is suitable for electrosurgery in addition to instrument channel sterilization is shown in FIG. 13. The probe tip 402 comprises a dielectric block 416 that has layers of metallization on its upper and lower surfaces. The inner conductor 418 of the coaxial cable 406 protrudes from the distal end of the coaxial cable 406 and is electrically bonded (e.g. using solder) to the upper layer of metallization (first electrode). The outer conductor of the coaxial cable 406 is electrically coupled to the lower layer of metallization (second electrode) by a braid termination 420. The braid termination 420 comprises a tubular part that is electrically bonded to the outer conductor and a distally extending plate part that fits under the dielectric block 416 and is electrically connected to the lower layer of metallization.

In this embodiment, a shaped piece of dielectric material 422 is attached to the lower surface of the dielectric block 416. It may be secured to the lower layer of metallization. The shaped piece of dielectric material 422 is curved such that in cross-section its lower surface describes the chord of a circle between the edges of the dielectric block 416. In the longitudinal direction, the shaped piece of dielectric material 422 comprises a proximal part with a constant cross-section and a distal part in which the underside gradually tapers (e.g. in a curved manner) towards the dielectric block 416.

In this embodiment, the gas conduit 408 terminates with a needle 424 (e.g. a hypodermic needle) which has an outer diameter smaller than the gas conduit 408 and which terminates with a sharp point. The needle 424 is retained in a longitudinal bore hole 426 through the shaped piece of dielectric material 422. Longitudinal movement of the gas conduit 408 relative to the dielectric block 416 acts to extend and retract the needle 424 from the probe tip.

Figure 14:
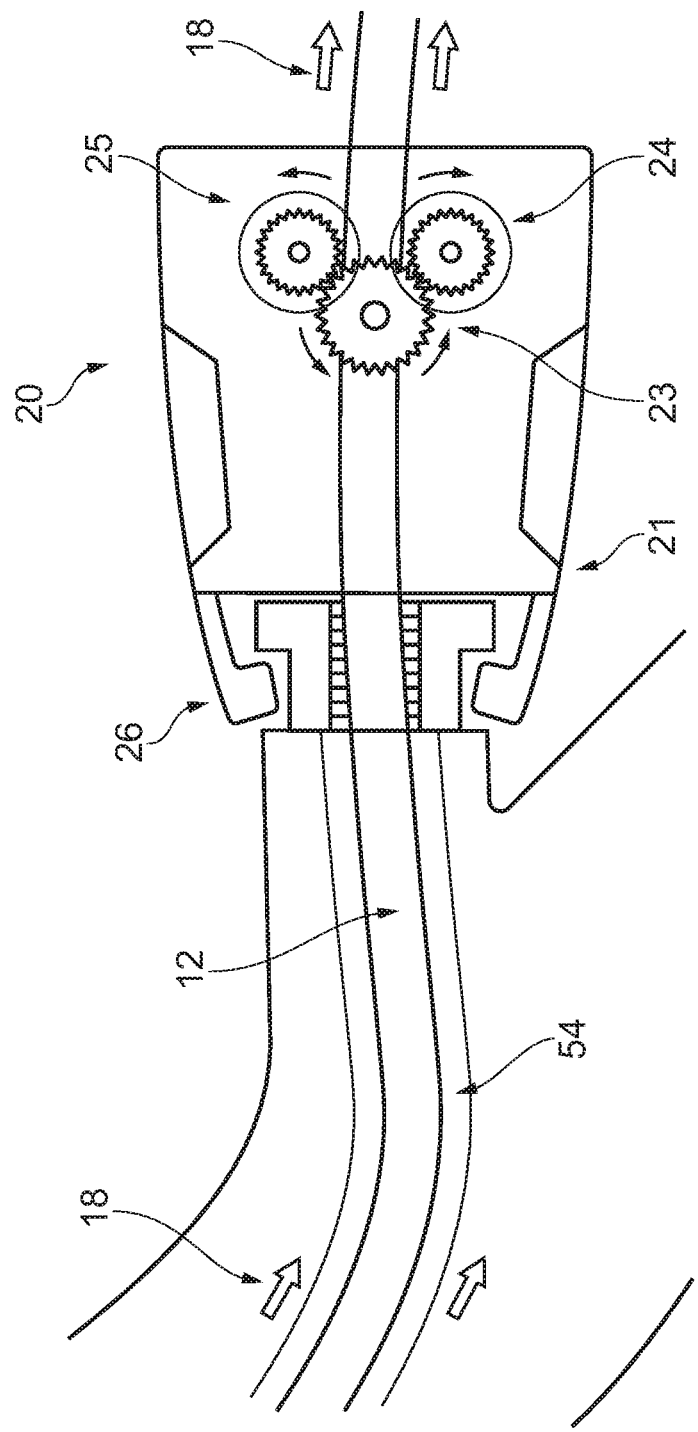
FIG. 14 is a longitudinal cross-sectional view through a withdrawal device that can be used with the present invention.

A cross-section through the withdrawal device 20 positioned on the handle of a scoping device 50 is shown in FIG. 14. The withdrawal device 20 is able to withdraw a coaxial cable 12 from an instrument channel 54, in a direction shown by arrows 18, at a predetermined rate. The withdrawal device 20 comprises a housing 21 containing a motor (not shown) and two rollers 25, wherein the motor acts to rotate rollers 25 via cogs 23, 24. The first cog 23 may be directly powered by the motor, and transfers rotational movement to the rollers 25 through a second cog 24 on each roller. The coaxial cable 12 is gripped between the rollers 25 such that it is withdrawn from the instrument channel 54 as the rollers 25 rotate.

The withdrawal device 20 is releasably attached to the scoping device 50 by an attachment portion 26. By attaching the withdrawal device 20 directly to the scoping device 50, it is ensured that the rotation of the rollers 25 acts to withdraw the coaxial cable 12 rather than move the device body along the cable. The withdrawal device 20 can therefore be set up to withdraw the coaxial cable without further user interaction during the process.

The withdrawal device 20 can also be configured to run in a 'reverse' mode to insert the coaxial cable 12 through the instrument channel 54. The reverse mode may be selected by a user through a switch on the housing 21 of the device. In addition, the rate of withdrawal or insertion is set by the speed of the motor. However, the speed of the motor may be adjustable. For example, the motor may comprise a control device for setting the speed. This may be adjusted by a control knob on the housing of the device. In alternative embodiments, the operation mode (forward/reverse) and speed of the motor may be set by a microcontroller which is part of the control device. The microcontroller may itself receive inputs from an external processing device, e.g. a Raspberry Pi® or Arduino® device.

Figure 15:
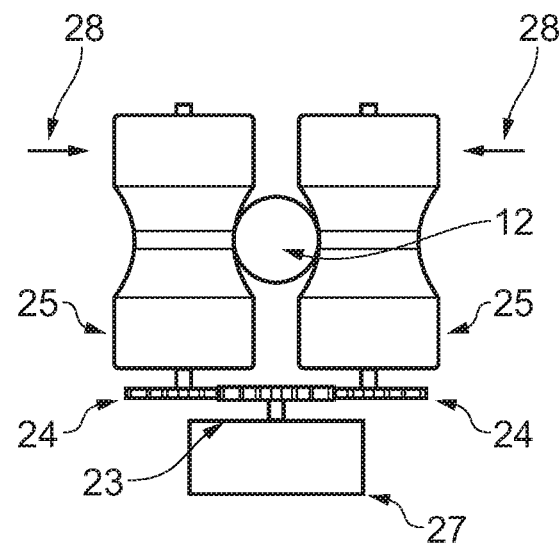
FIG. 15 is a lateral cross-sectional view through driving components in the withdrawal device of FIG. 14.

FIG. 15 shows a cross-section through the motor 27; cogs 23, 24; rollers 25 and instrument cable 12. As can be seen in the figure, the rollers 25 have an hourglass cross-sectional shape which gives a good fit between the rollers and the instrument cable, increasing friction to ensure that the coaxial cable 12 is smoothly pulled by rotation of the rollers 25. The rollers 25 may be made of a silicone material which conforms to the surface shape of the coaxial cable 12. In addition, the rollers 25 are biased towards each other, in a direction shown by arrows 28, to ensure good contact between the rollers 25 and the surface of the coaxial cable 12.

Figure 16:
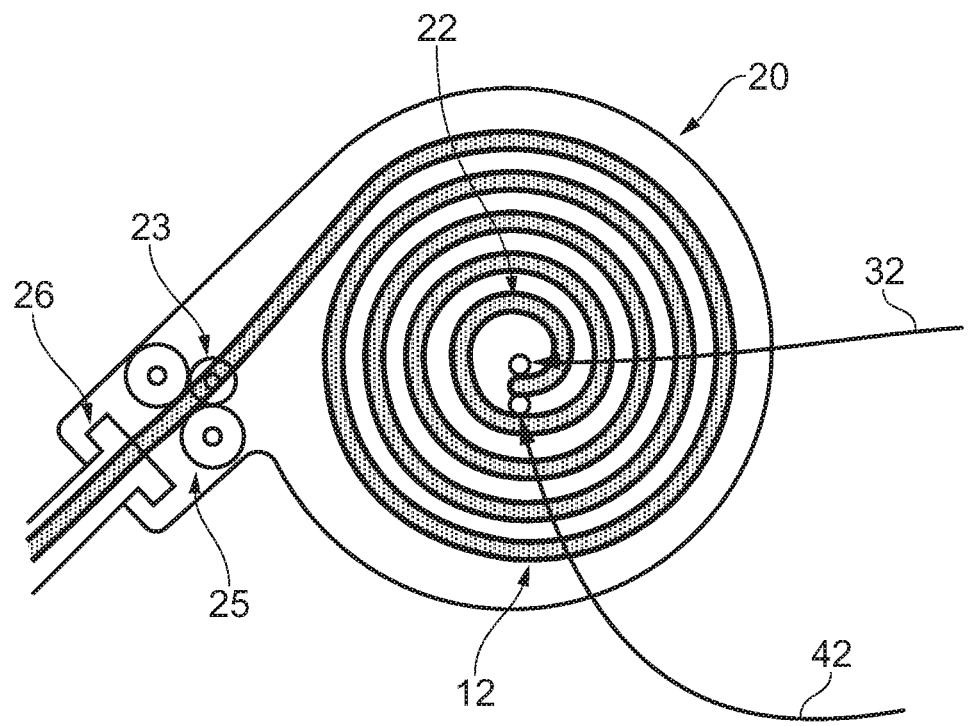
FIG. 16 is a longitudinal cross-sectional view through another withdrawal device that can be used with the present invention.

FIG. 16 shows a view of an alternative embodiment of a withdrawal device 20. In this embodiment, the withdrawal device 20 further comprises a drum 22 around which the coaxial cable 12 is wrapped as it is withdrawn from the instrument channel of a scoping device. The drum 22 may have a spring drive mechanism to automatically wind the coaxial cable 12 about the drum as it is withdrawn by action of the rollers 25. Gas and RF and/or microwave EM energy are provided to the coaxial cable 12 via a connecting tube 42 and a connecting wire 32, which may respectively be connected to a gas supply and a generator (not shown). These connections mean that the probe tip at the distal end of the coaxial cable 12 is able to carry out sterilization of the instrument channel as it is withdrawn by the withdrawal device 20.

The drum 22 may also be used to store the coaxial cable 12 before it inserted into an instrument channel by the same motor and roller mechanism discussed above. The drum and housing may provide a sterile environment, as well as providing a space saving storage place for the cable 12.

FIGS. 17A-17C show a sterilization apparatus in use for sterilizing the instrument channel of a scoping device 50. In FIG. 17A, the scoping device 50 is hung from a stand 60 so that the insertion tube 52 hangs vertically downwards. The coaxial cable 12 of an elongate sterilization instrument is fully inserted in the instrument channel within the insertion tube. A withdrawal device 20 is attached to the scoping device 50, and is positioned on the coaxial cable 12 towards its proximal end. A generator 30 is configured to provide RF and/or microwave frequency EM radiation to the elongate instrument via connecting wire 32. A gas supply 40 is configured to supply a gas, e.g. Argon, to the elongate instrument via a connecting tube 42.

In FIG. 17B, the motor of the withdrawal device 20 has been switched on to withdraw the coaxial cable 12 from the instrument channel of the scoping device 50 at a predetermined rate. At the same time, a probe tip (not shown) at the distal end of the coaxial cable 12 is generating a non-thermal plasma to sterilize the instrument channel. The plasma is generated at the probe tip by producing an electric field from the received RF and/or microwave frequency EM energy across a flow path of gas received from the gas supply 40. The gas reaches the probe tip through a gas conduit which extends the length of the elongate instrument.

FIG. 17C shows the apparatus when the coaxial cable 12 has been completely withdrawn from the instrument channel. At this point the instrument channel is completely sterilised, requiring no further processing such as rinsing. The coaxial cable 12 and insertion tube 52 both hang vertically downwards from the stand 60, which avoids contamination by contact with other surfaces. The withdrawal device 20 remains attached to the scoping device 50. The generator 30 and gas supply 40 can be switched off as there is no further need for plasma to be produced at the probe tip.

Figure 18:
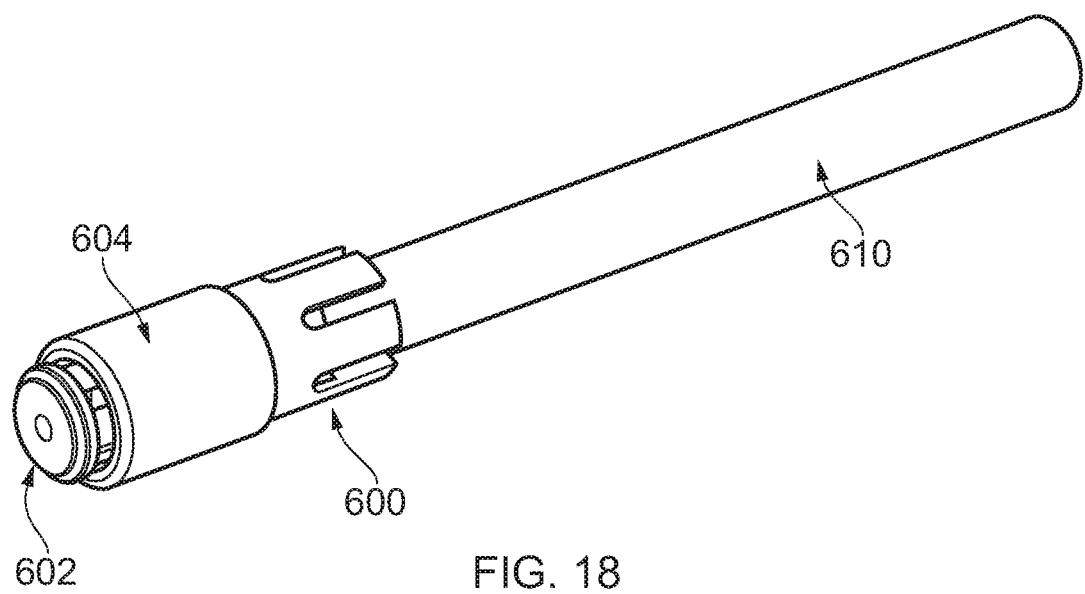
FIG. 18 is a schematic view of a probe tip which may be used with the present invention.

FIG. 18 shows a plan view of a probe tip 600, suitable for sterilization of an instrument channel, connected to the distal end of a coaxial cable 610. The probe tip is configured to produce a circumferential jet of thermal or non-thermal plasma which can be directed at the wall of the instrument channel as the elongate instrument is withdrawn. In this embodiment, the first electrode 602 is a circular plate of conducting material, such as copper, which is connected to the inner conductor of the coaxial cable 610. The second electrode 604 is a cylinder of conducting material, e.g. copper, connected to the outer conductor of the coaxial cable 610. Between the second electrode 604 and the inner conductor there is a dielectric element, wherein the first electrode 602 is mounted on the end of the dielectric element. There is an annular opening between the first and second electrodes which defines the end of the gas conduit and out of which a thermal or non-thermal plasma is emitted when in use. The elongate instrument comprises a sleeve (not shown) which surrounds the coaxial cable from a proximal to a distal end of the instrument so as to define a gas conduit between the sleeve and the outer surface of the coaxial cable 610.

Figure 19:
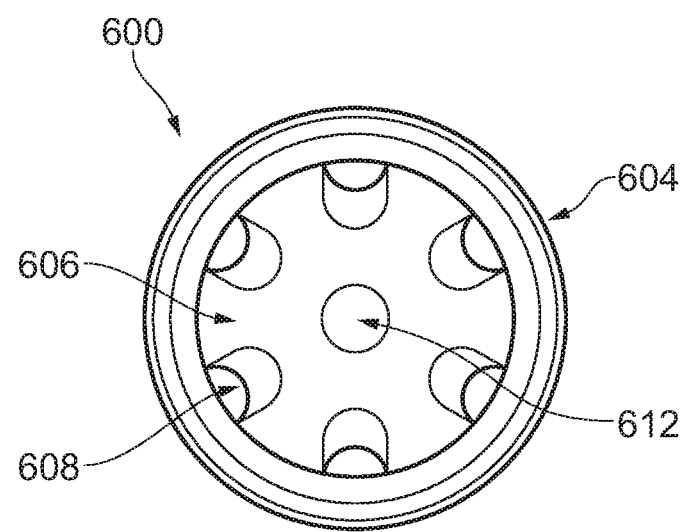
FIG. 19 is an end view of the probe tip of FIG. 18.

FIG. 19 shows an end view of the probe tip 600 of FIG. 18 with the first electrode 602 removed. As can be seen in FIG. 19, the dielectric element 606 is positioned between the second electrode 604 and the inner conductor 612 of the coaxial cable 610. There are a number of groove 608 in the outer surface of the dielectric element 606 where gas is subjected to an electric field to produce a thermal or non-thermal plasma which is then emitted from the probe tip 600. The equally spaced grooves 608 help ensure that the plasma is emitted circumferentially and directed at the walls of the instrument channel. The dielectric element 606 may be elongate such that it has a length substantially equal to that of the second electrode 604.

The invention claimed is:

1. A sterilization apparatus for sterilizing an instrument channel of a surgical scoping device, the apparatus comprising:
   a sterilization instrument configured to be inserted through the instrument channel of a surgical scoping device, the sterilization instrument comprising:
      an elongate probe comprising a coaxial cable for conveying radiofrequency (RF) electromagnetic (EM) energy and/or microwave EM energy, and a probe tip connected at the distal end of the coaxial cable for receiving the RF and/or microwave energy,
      wherein the coaxial cable comprises an inner conductor, an outer conductor and a dielectric material separating the inner conductor from the outer conductor,
      wherein the probe tip comprises a first electrode connected to the inner conductor of the coaxial cable and a second electrode connected to the outer conductor of the coaxial cable, and
      wherein the first electrode and second electrode are arranged to produce an electric field from the received RF and/or microwave frequency EM energy; and
   a withdrawal device for withdrawing the sterilization instrument from the instrument channel at a predetermined rate.

2. A sterilization apparatus according to claim 1, wherein the sterilization instrument is further configured to be extendable out of the instrument channel to deliver the RF EM energy and/or the microwave EM energy into biological tissue located at a distal end of the instrument channel.

3. A sterilization apparatus according to claim 1, wherein the sterilization instrument further comprises a gas conduit for conveying gas to the probe tip, and
   wherein the first electrode and second electrode are arranged to produce an electric field from the received RF and/or microwave frequency EM energy across a flow path of gas received from the gas conduit to produce a thermal plasma or a non-thermal plasma.

4. A sterilization apparatus according to claim 3, wherein the coaxial cable has a lumen extending from a proximal end to a distal end of the cable, wherein the lumen forms the gas conduit for conveying gas through the elongate probe to the probe tip.

5. A sterilization apparatus according to claim 3, wherein the gas conduit passes through the probe tip.

6. A sterilization apparatus according to claim 3, wherein the probe tip is a plasma applicator having an enclosed plasma generating region and an outlet for directing plasma out of the plasma generating region towards an inner surface of the instrument channel.

7. A sterilization apparatus according to claim 3, wherein the coaxial cable comprises a layered structure comprising:
   an innermost insulating layer;
   an inner conductive layer formed on the innermost insulating layer;
   an outer conductive layer formed coaxially with the inner conductive layer; and
   a dielectric layer separating the inner conductive layer and the outer conductive layer,
   wherein the inner conductive layer, the outer conductive layer and the dielectric layer form a transmission line for conveying RF and/or microwave frequency energy, and wherein the innermost insulating layer is hollow, thereby providing a longitudinal channel within the coaxial cable.

8. A sterilization apparatus according to claim 7, wherein the coaxial cable further comprises
   a first terminal that is electrically connected to the inner conductive layer and which extends through the innermost insulating layer into the channel; and
   a second terminal that is electrically connected to the outer conductive layer and which extends through the dielectric layer and innermost insulating layer into the channel;
   wherein the first terminal and the second terminal may be arranged to form electrical connection with the first and second electrodes on the probe tip, wherein
   the probe tip is insertable in or through the longitudinal channel.

9. A sterilization apparatus according to claim 7, wherein the probe tip comprises:
   an extension of the innermost insulating layer of the coaxial cable;
   the first electrode, comprising an extension of the inner conductive layer of the coaxial cable;
   a dielectric cylinder placed over the inner conductive layer; and
   the second electrode, comprising a metal tube which is electrically connected to the outer conductive layer of the coaxial cable.

10. A sterilization apparatus according to claim 9, wherein the dielectric cylinder comprises a number of holes in the walls of the cylinder.

11. A sterilization apparatus according to claim 7, wherein the longitudinal channel comprises or contains the gas conduit.

12. A sterilization apparatus according to claim 1, wherein the probe tip comprises a single piece of metallized dielectric material.

13. A sterilization apparatus according to claim 1, wherein the probe tip has a parallel plate structure comprising:
   a substantially planar body of dielectric material;
   a first conductive layer on a first surface of the planar body as the first electrode; and
   a second conductive layer on a second surface of the planar body that is opposite to the first surface, as the second electrode.

14. A sterilization apparatus according to claim 1 further comprising:
  a container defining a sterilization enclosure for the surgical scoping device, and
  a plasma generating unit for creating a non-thermal plasma or a thermal plasma within the sterilization enclosure for sterilizing an exterior surface of the surgical scoping device,
  wherein the container includes a chamber for receiving a control head of the surgical scoping device, and
  wherein the plasma generating unit includes an annular body for enclosing an instrument tube of the surgical scoping device.

15. A sterilization apparatus according to claim 1, wherein the probe tip further comprises a cleaning brush.

16. A sterilization apparatus according to claim 1, wherein the predetermined rate is less than 10 mm per second.

17. A sterilization apparatus according to claim 1, wherein the withdrawal device comprises:
  a cable coupling element operably connected to the elongate probe at a proximal end thereof; and
  a motor arranged to drive the cable coupling element to cause relative movement between the elongate probe and the instrument channel in a longitudinal direction.

18. A sterilization apparatus according to claim 17, wherein the cable coupling element comprises a plurality of rollers defining a space between them for receiving the elongate probe, the rollers being arranged to grip an exterior surface of the elongate probe whereby rotation of the rollers causes longitudinal movement of the elongate probe.

19. A sterilization apparatus according to claim 18, wherein the motor is disengagable from the cable coupling element.

20. A probe withdrawal device for moving an elongate probe through an instrument channel of a surgical scoping device, the probe withdrawal device comprising:
  a cable coupling element operably connected to the elongate probe at a proximal end thereof; and
  a motor arranged to drive the cable coupling element to cause relative movement at a predetermined rate between the elongate probe and the instrument channel in a longitudinal direction.

* * * * *